(12) United States Patent
Tanaka et al.

(10) Patent No.: US 12,286,107 B2
(45) Date of Patent: Apr. 29, 2025

(54) OPERATION SUPPORT METHOD, OPERATION SUPPORT SYSTEM, AND OPERATION SUPPORT SERVER

(71) Applicant: LOGISTEED, Ltd., Tokyo (JP)

(72) Inventors: Takeshi Tanaka, Tokyo (JP); Shunsuke Minusa, Tokyo (JP); Hiroyuki Kuriyama, Tokyo (JP); Daichi Ojiro, Tokyo (JP); Kiminori Sato, Tokyo (JP)

(73) Assignee: LOGISTEED, Ltd., Tokyo (JP)

( * ) Notice: Subject to any disclaimer, the term of this patent is extended or adjusted under 35 U.S.C. 154(b) by 214 days.

(21) Appl. No.: 17/928,046

(22) PCT Filed: Jun. 7, 2021

(86) PCT No.: PCT/JP2021/021634
§ 371 (c)(1),
(2) Date: Nov. 28, 2022

(87) PCT Pub. No.: WO2021/251351
PCT Pub. Date: Dec. 16, 2021

(65) Prior Publication Data
US 2023/0211780 A1 Jul. 6, 2023

(30) Foreign Application Priority Data

Jun. 9, 2020 (JP) ................................ 2020-100060
Sep. 18, 2020 (JP) ................................ 2020-157573

(51) Int. Cl.
*B60W 30/095* (2012.01)
*A61B 5/00* (2006.01)
(Continued)

(52) U.S. Cl.
CPC ..... *B60W 30/0956* (2013.01); *A61B 5/02405* (2013.01); *A61B 5/352* (2021.01);
(Continued)

(58) Field of Classification Search
CPC ............ B60W 30/0956; B60W 40/08; B60W 50/0097; B60W 50/14; B60W 2556/10;
(Continued)

(56) References Cited

U.S. PATENT DOCUMENTS 9,293,042 B1 * 3/2016 Wasserman ............... G08G 1/09
10,399,495 B1 * 9/2019 Osborne ................ B60Q 9/008
(Continued)

FOREIGN PATENT DOCUMENTS

| JP | 2009-098970 A | 5/2009 |
| JP | 2009-245147 A | 10/2009 |
| WO | 2017/038166 A1 | 3/2017 |

*Primary Examiner* — Naomi J Small
(74) *Attorney, Agent, or Firm* — Volpe Koenig

(57) ABSTRACT

A computer generates an accident risk definition model to estimate a probability of hazard occurrence as an accident risk by inputting first in-vehicle sensor data collected in the past and hazard occurrence data having information on hazard occurrence from the first in-vehicle sensor data preset therein, generates accident risk estimation data by inputting second in-vehicle sensor data collected in the past to the accident risk definition model and estimating the probability of the hazard occurrence, generates an accident risk prediction model to predict the accident risk after a predetermined time by inputting first biological index data corresponding to the second in-vehicle sensor data and the accident risk estimation data, calculates second biological index data from second biological sensor data by acquiring the second biological sensor data of a driver, and predicts the accident risk after the predetermined time by inputting second biological index data to the accident risk prediction model.

35 Claims, 29 Drawing Sheets

(51) Int. Cl.
  *A61B 5/024*  (2006.01)
  *A61B 5/352*  (2021.01)
  *B60W 40/08*  (2012.01)
  *B60W 50/00*  (2006.01)
  *B60W 50/14*  (2020.01)
  *G06N 20/00*  (2019.01)

(52) U.S. Cl.
  CPC ............ *A61B 5/7257* (2013.01); *B60W 40/08* (2013.01); *B60W 50/0097* (2013.01); *B60W 50/14* (2013.01); *G06N 20/00* (2019.01); *B60W 2050/146* (2013.01); *B60W 2540/221* (2020.02); *B60W 2556/10* (2020.02); *B60W 2556/50* (2020.02)

(58) Field of Classification Search
  CPC ....... B60W 2556/50; B60W 2540/221; B60W 2050/146; G06N 20/00; A61B 5/352; A61B 5/02405; A61B 5/7257
  USPC ......................................................... 340/576
  See application file for complete search history.

(56) References Cited

U.S. PATENT DOCUMENTS

| | | | |
|---|---|---|---|
| 10,540,892 B1 * | 1/2020 | Fields | G07C 5/0841 |
| 2016/0047666 A1 * | 2/2016 | Fuchs | G06Q 40/08 |
| | | | 701/423 |
| 2017/0057411 A1 * | 3/2017 | Heath | G08G 1/0112 |
| 2018/0170372 A1 * | 6/2018 | Takamatsu | G08G 1/096725 |
| 2020/0057487 A1 * | 2/2020 | Sicconi | G06F 3/011 |
| 2020/0090426 A1 * | 3/2020 | Barnes | G07C 5/085 |
| 2021/0394751 A1 | 12/2021 | Takamatu et al. | |

\* cited by examiner

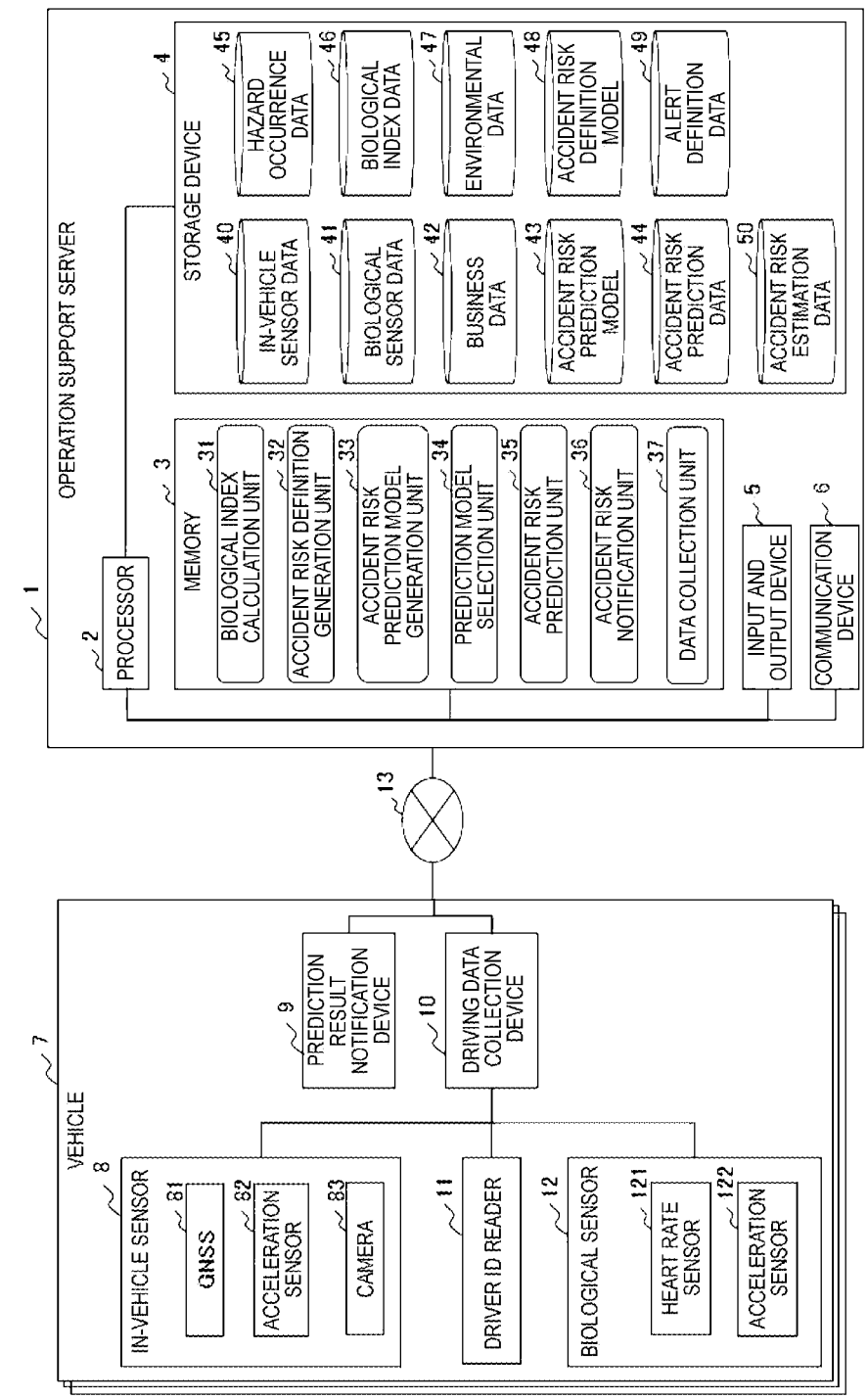
[FIG. 1]

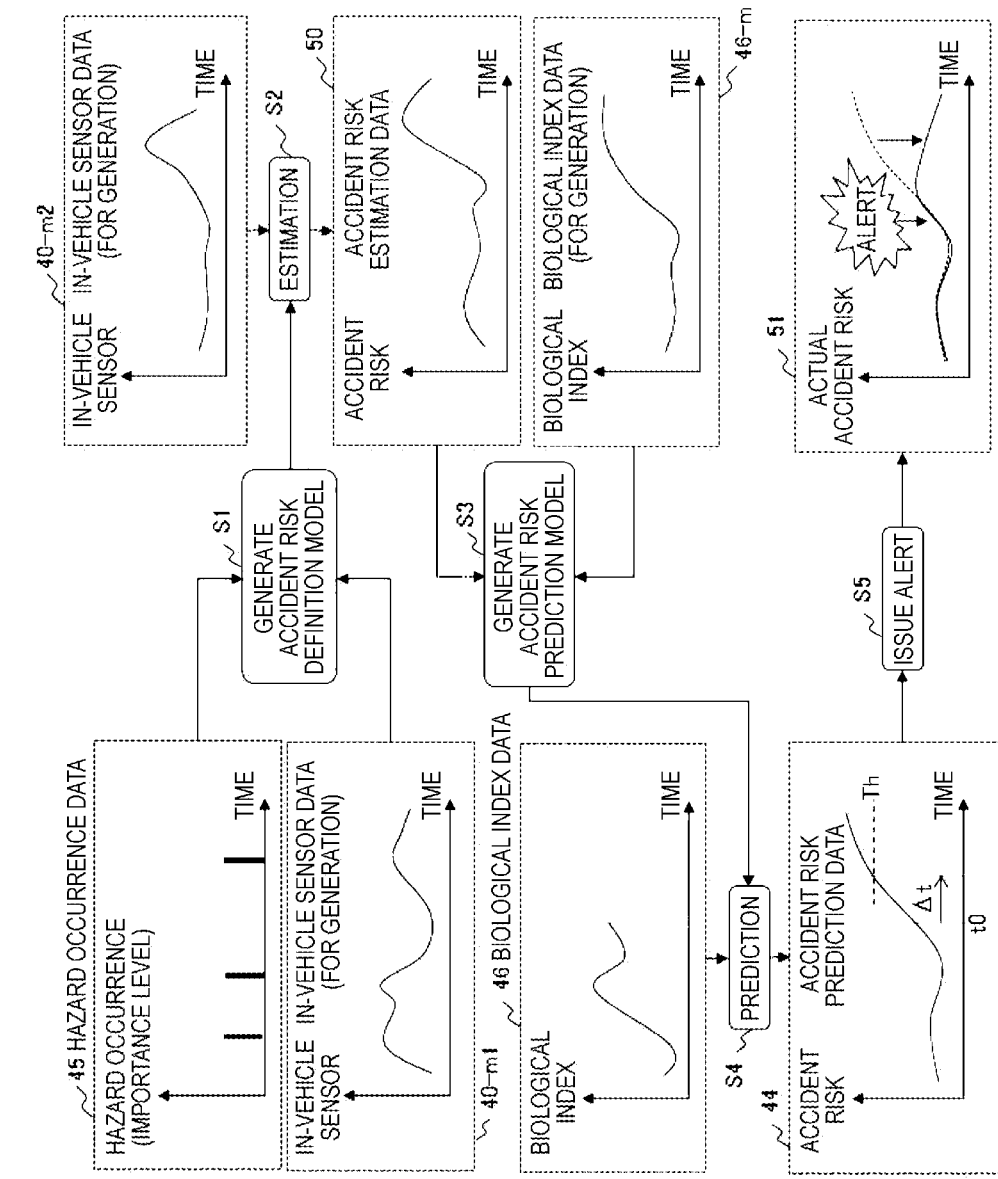
[FIG. 2]

[FIG. 3]
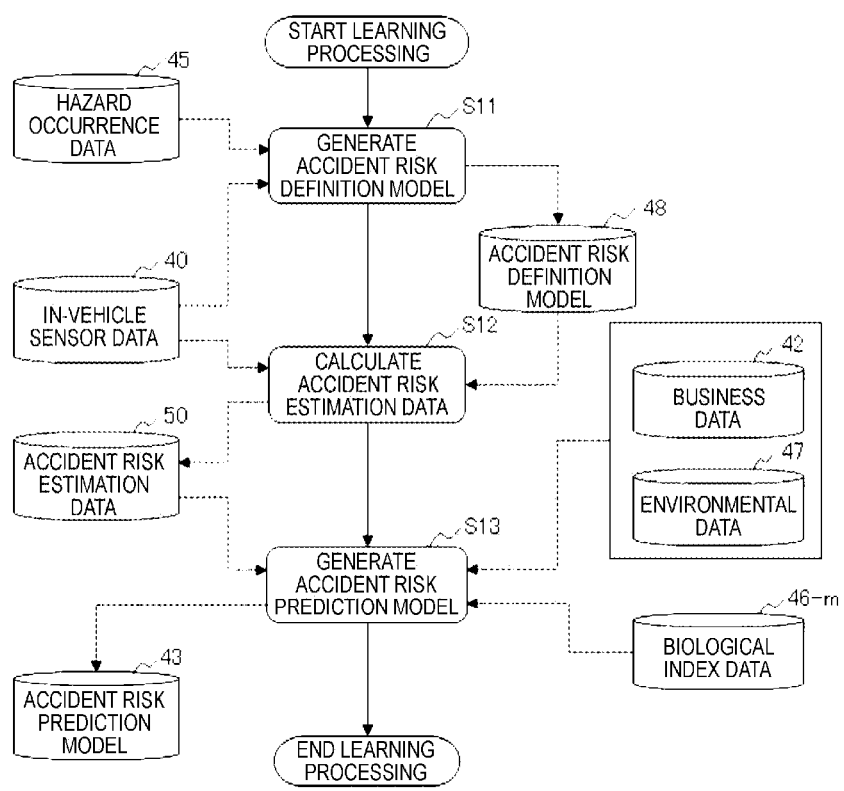

[FIG. 4]
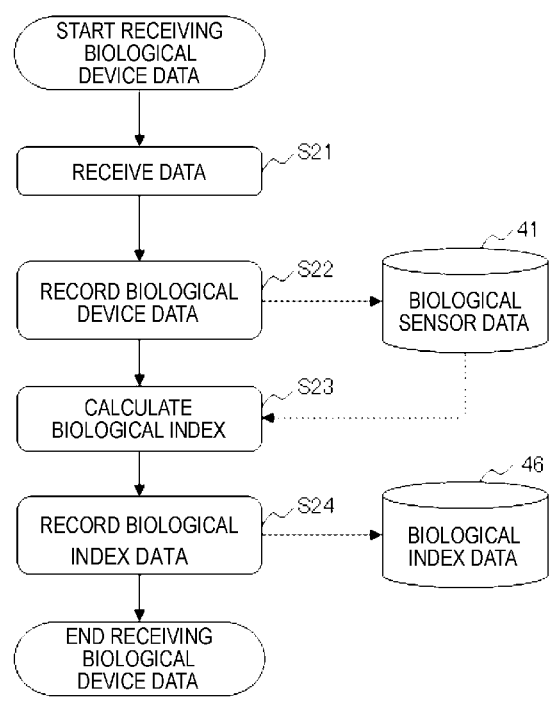

[FIG. 5]
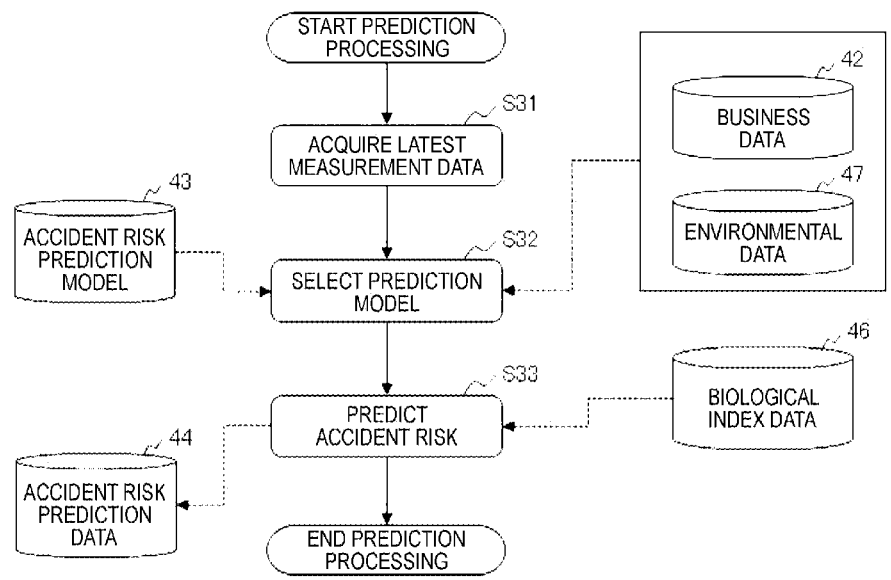

[FIG. 6]
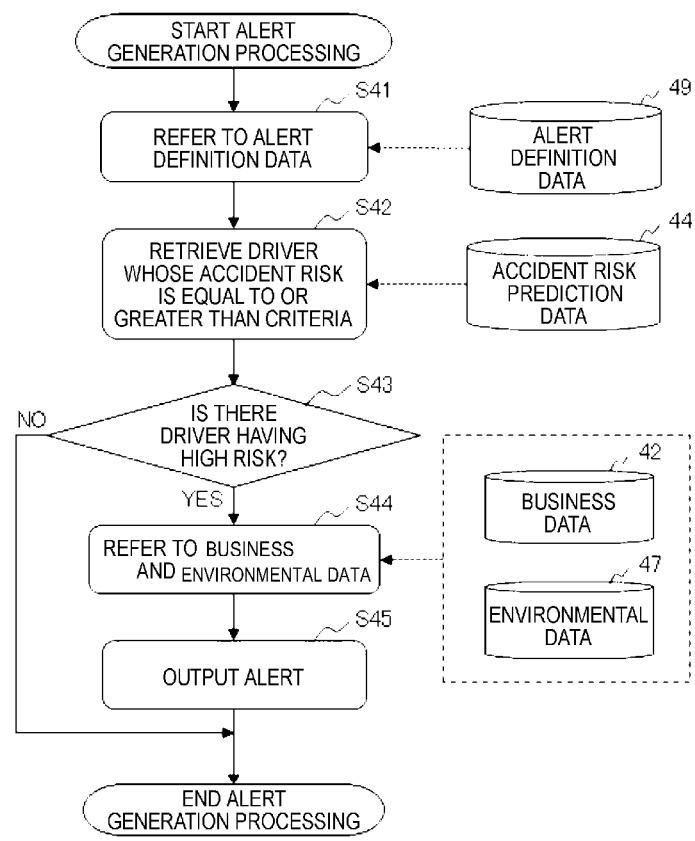

[FIG. 7A]
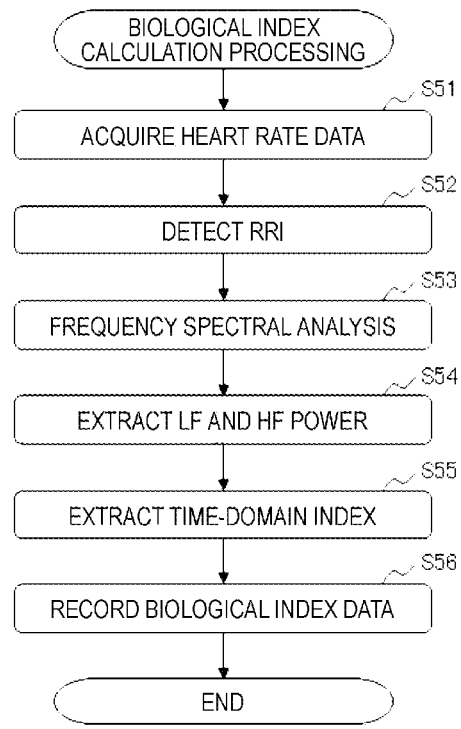
[FIG. 7B]
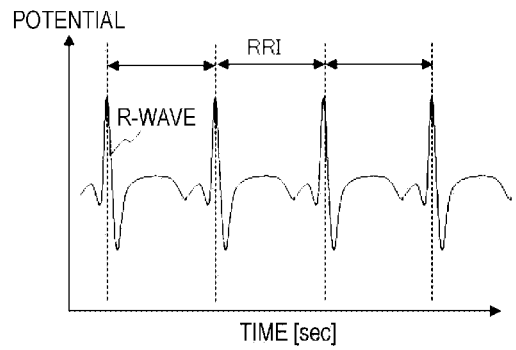

[FIG. 7C]
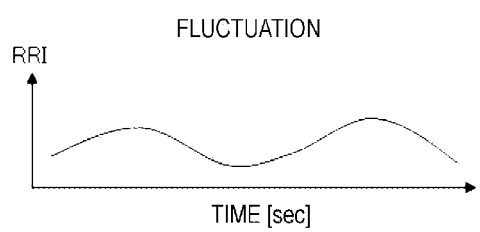
[FIG. 7D]
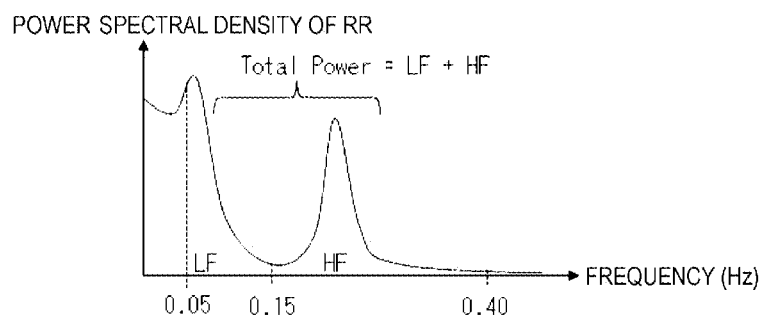
[FIG. 7E]
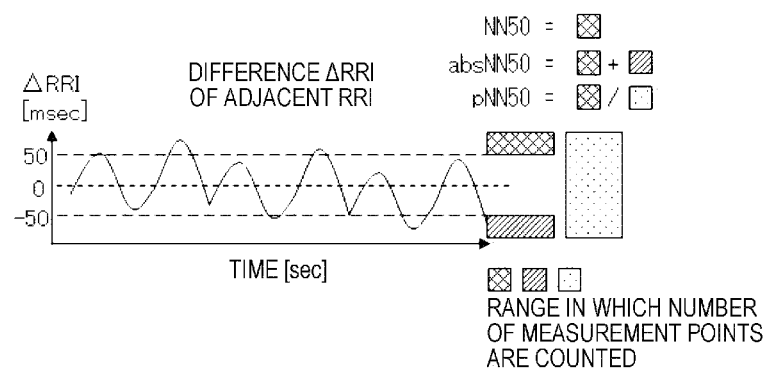

[FIG. 8]

46 BIOLOGICAL INDEX DATA

| USER ID | DATE AND TIME | AUTONOMIC NERVE TOTAL POWER | AUTONOMIC NERVE LF/HF | AUTONOMIC NERVE NN50 | ... | AVERAGE RRI |
|---|---|---|---|---|---|---|
| 00000001 | 2019/12/21 9:30:00 | 12.5 | 1.2 | 0 | ... | 0.81 |
| 00000001 | 2019/12/21 9:31:00 | 12.8 | 3.5 | 1 | ... | 0.82 |
| ... | ... | ... | ... | ... | ... | ... |

42 BUSINESS DATA

| USER ID | START DATE AND TIME | END DATE AND TIME | VEHICLE ID | ... | BUSINESS TYPE |
|---|---|---|---|---|---|
| 00000001 | 2019/12/21 8:35:00 | 2019/12/21 12:10:00 | 01AB | ... | DRIVING |
| 00000001 | 2019/12/21 12:10:00 | 2019/12/21 12:40:00 | 01AB | ... | RESTING |
| ... | ... | ... | ... | ... | ... |

47 ENVIRONMENTAL DATA

| VEHICLE ID | DATE AND TIME | TRAFFIC JAM STATUS | WEATHER | ... | TEMPERATURE |
|---|---|---|---|---|---|
| 01AB | 2019/12/21 10:20:00 | NO TRAFFIC JAM | GOOD WEATHER | ... | 11 |
| 01AB | 2019/12/21 10:30:00 | NO TRAFFIC JAM | GOOD WEATHER | ... | 11 |
| ... | ... | ... | ... | ... | ... |

40 IN-VEHICLE SENSOR DATA

| 400 | 401 | 402 | 403 | ... | 404 |
|---|---|---|---|---|---|
| VEHICLE ID | DATE AND TIME | POSITION | SPEED | ... | ACCELERATION |
| 01AB | 2019/12/21 10:20:38 | 35° 42'43.9"N 139° 45'34.7"E | 41.2 | ... | 0.5 |
| 01AB | 2019/12/21 10:20:39 | 35° 42'43.9"N 139° 45'34.7"E | 41.3 | ... | 0.5 |
| ... | ... | ... | ... | ... | ... |

[FIG. 12]

45 HAZARD OCCURRENCE DATA

| 450 | 451 | 452 | 453 |
|---|---|---|---|
| VEHICLE ID | DATE AND TIME | HAZARD TYPE | IMPORTANCE LEVEL |
| 01AB | 2019/12/23 14:33:12 | LACK OF DISTANCE BETWEEN VEHICLES | 4 |
| 01AB | 2019/12/23 15:27:48 | OVERSPEED | 3 |
| ... | ... | ... | |

[FIG. 13]

50 ACCIDENT RISK ESTIMATION DATA

| 500 | 501 | 502 | 503 |
|---|---|---|---|
| USER ID | VEHICLE ID | DATE AND TIME | ACCIDENT RISK (%) |
| 00000001 | 01AB | 2019/12/21 10:20:00 | 34 |
| 00000001 | 01AB | 2019/12/21 10:21:00 | 36 |
| | | ... | ... |

[FIG. 14]

49 ALERT DEFINITION DATA

| ALERT ID | ACCIDENT RISK CONDITION | TIME CONDITION | TRAFFIC JAM CONDITION | WEATHER CONDITION | PRIORITY | COMMENT |
|---|---|---|---|---|---|---|
| 1 | 70 <= | - | - | - | 1 | YOU MAY BE TIRED. PLEASE, CAREFULLY AND SAFELY DRIVE YOUR VEHICLE AND TAKE EARLY BREAK |
| 2 | 60 <= | - | THERE IS TRAFFIC JAM | - | 2 | PAY ATTENTION TO DISTANCE FROM VEHICLE IN FRONT OF YOU WHILE DRIVING |
| 3 | 50 <= | - | NO TRAFFIC JAM | RAIN | 3 | PAY ATTENTION TO SPEED AND CURVE WHILE DRIVING |
| ... | | | ... | | | |

[FIG. 15]

44 ACCIDENT RISK PREDICTION DATA

| USER ID /440 | VEHICLE ID /441 | DATE AND TIME /442 | PREDICTED DATE AND TIME /443 | ACCIDENT RISK /444 |
|---|---|---|---|---|
| 00000001 | 01AB | 2020/1/12 13:48:00 | 2020/1/12 14:18:00 | 53 |
| 00000001 | 01AB | 2020/1/12 13:49:00 | 2019/12/21 14:29:00 | 61 |
| ... | ... | ... | ... | ... |

[FIG. 16A]
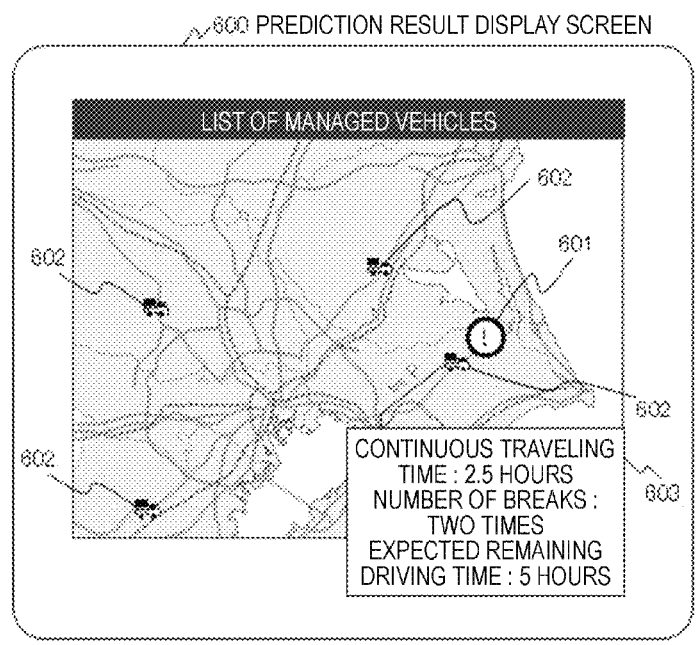
[FIG. 16B]
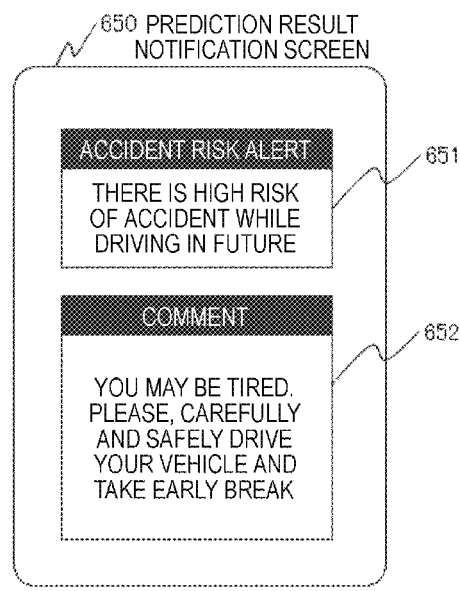

[FIG. 17]
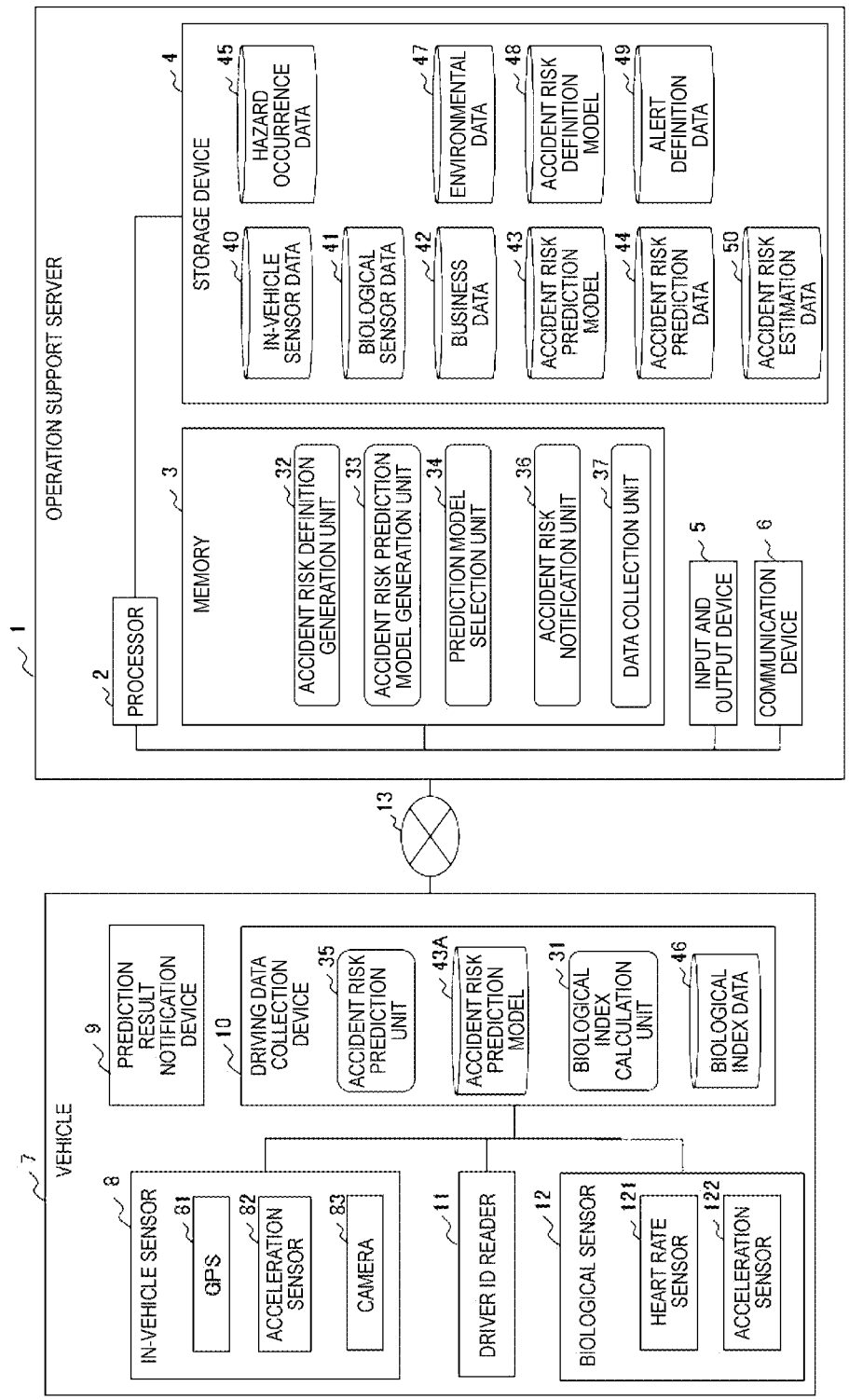

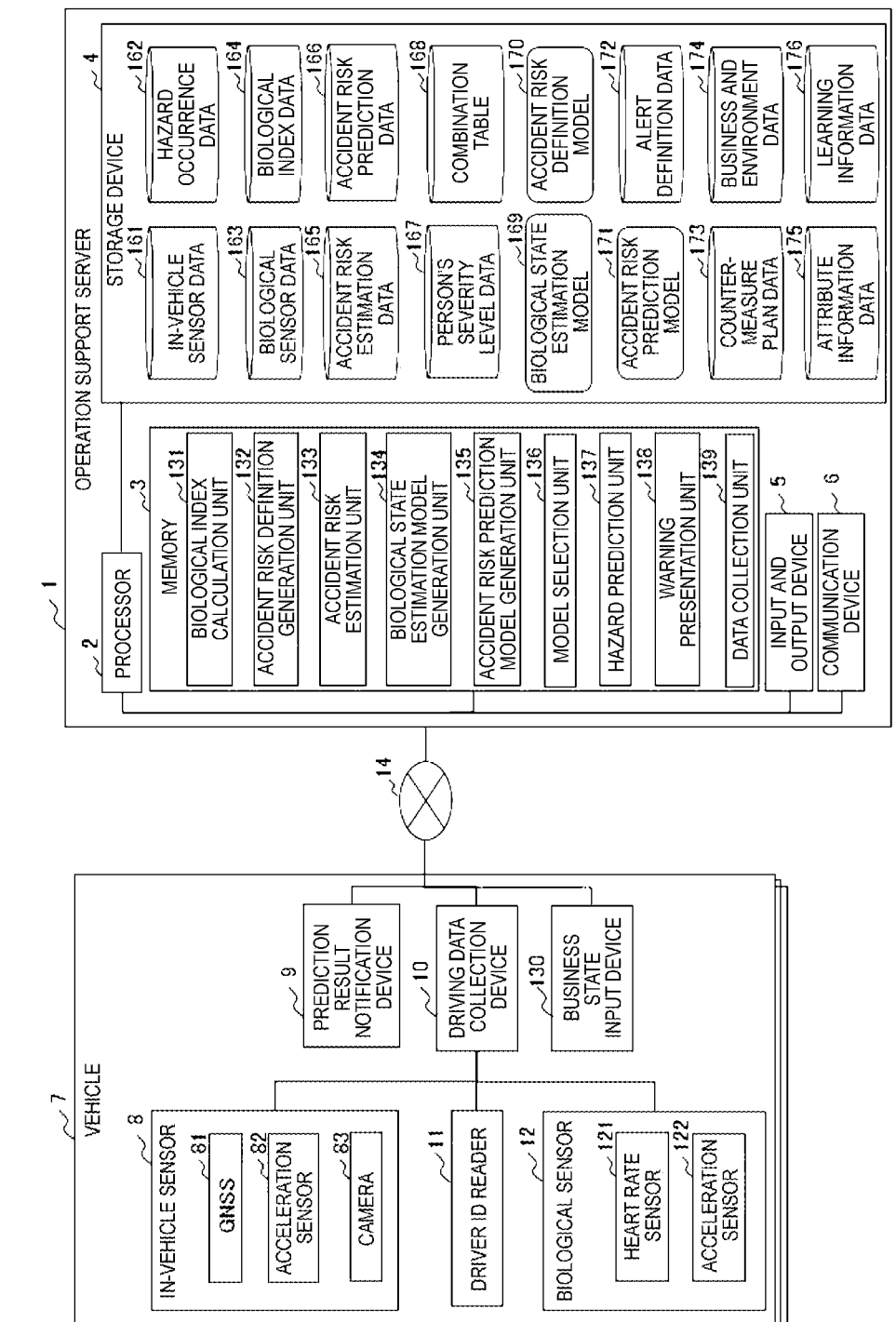
[FIG. 18]

[FIG. 19]
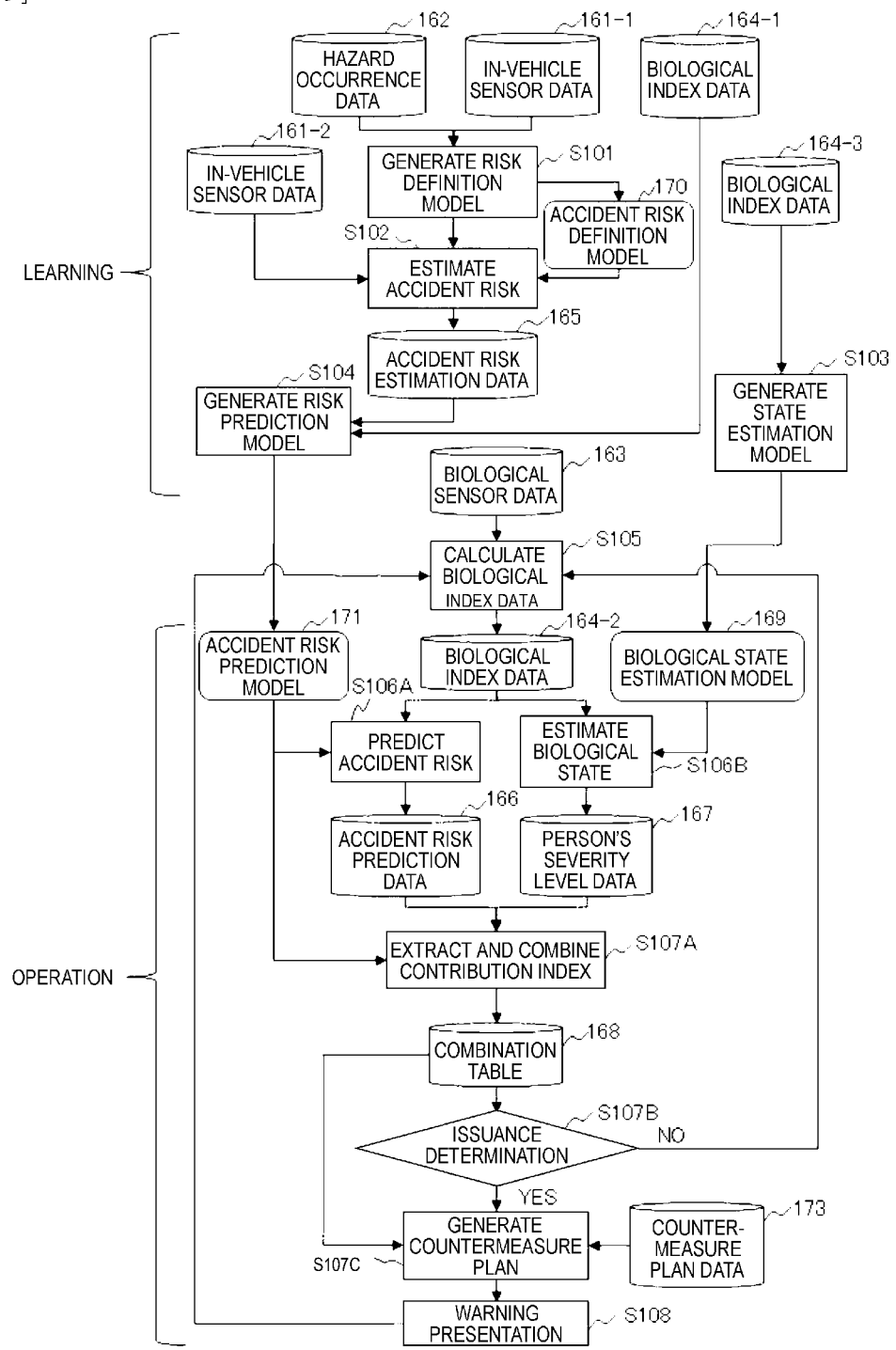

[FIG. 20]
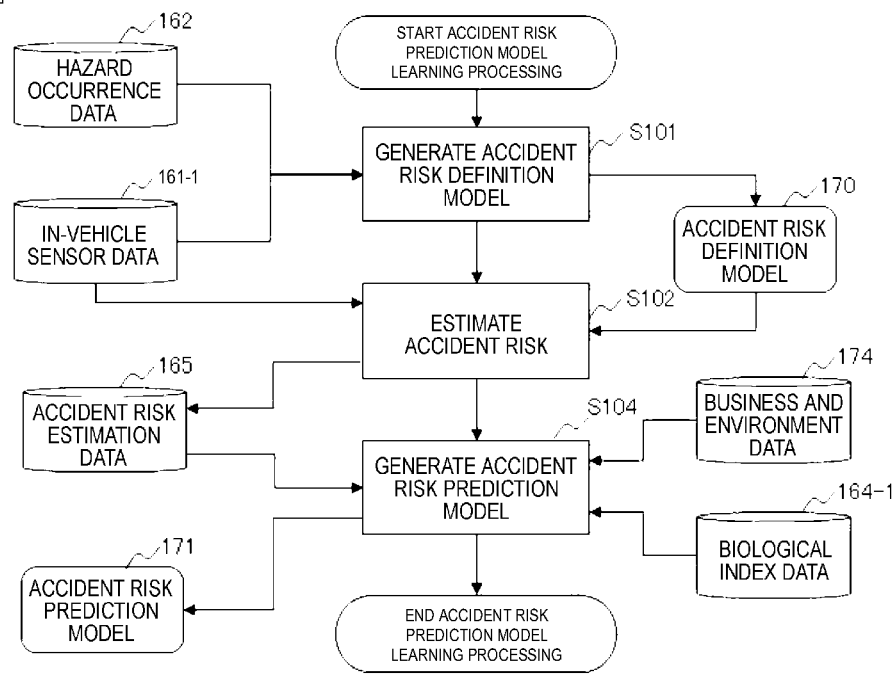
[FIG. 21]
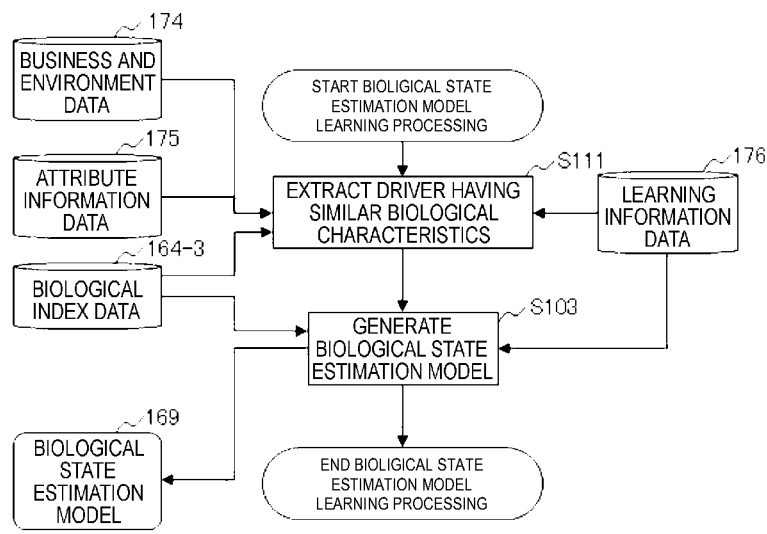

[FIG. 22]
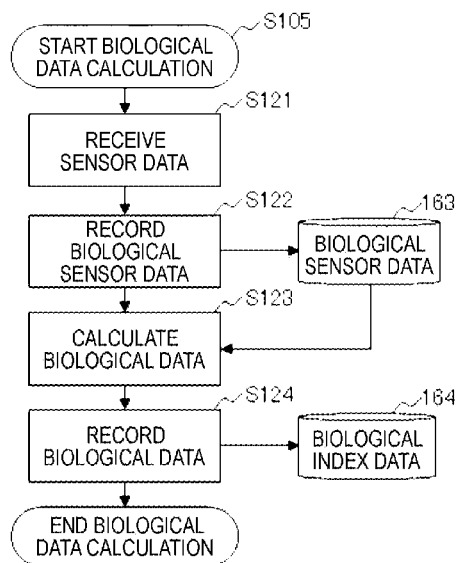
[FIG. 23]
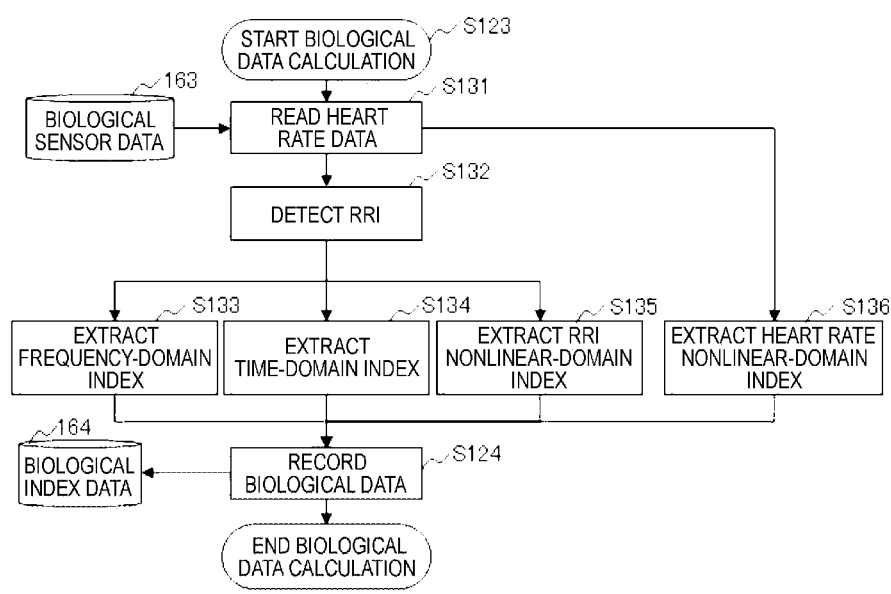

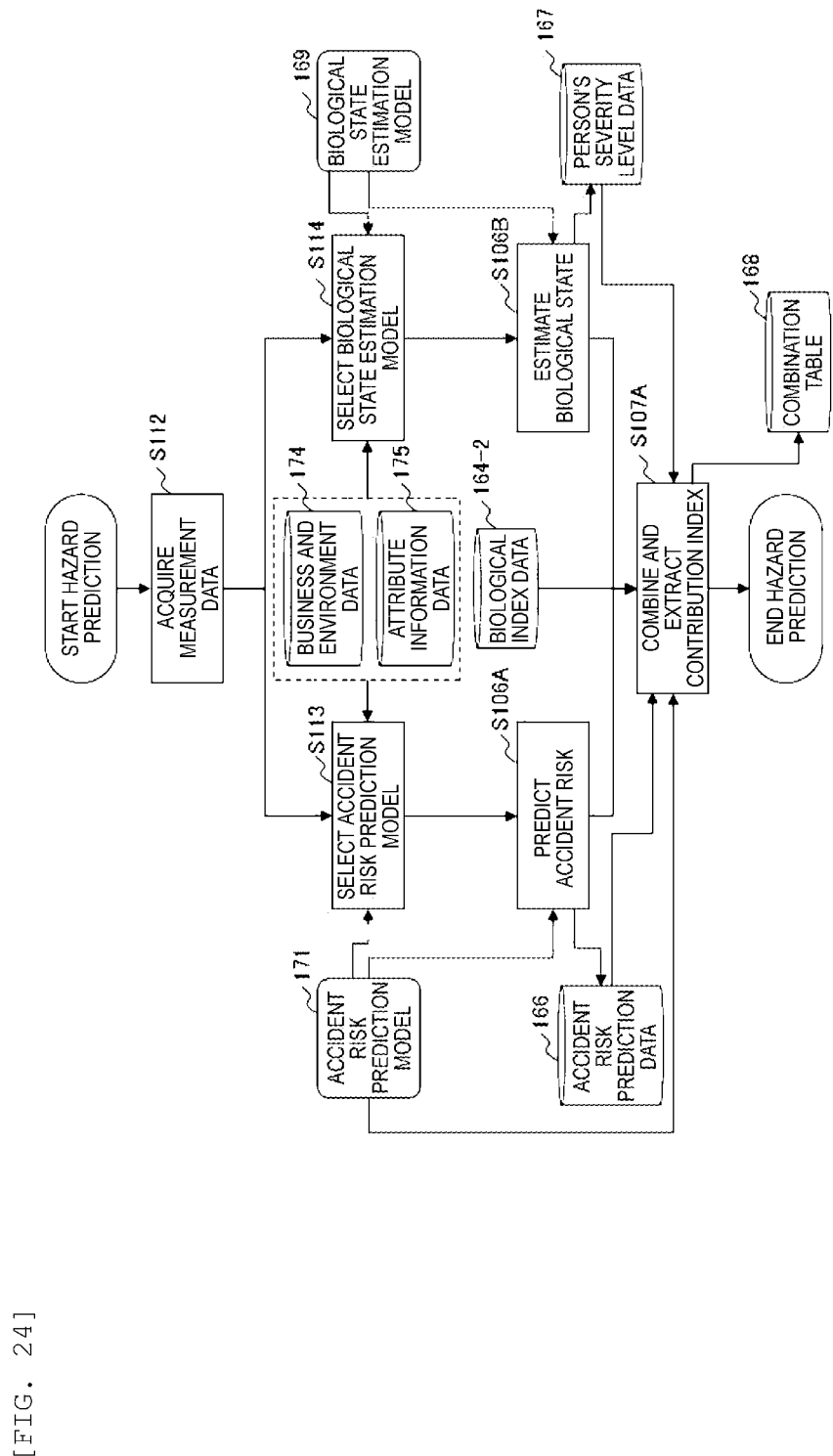
[FIG. 24]

[FIG. 25]
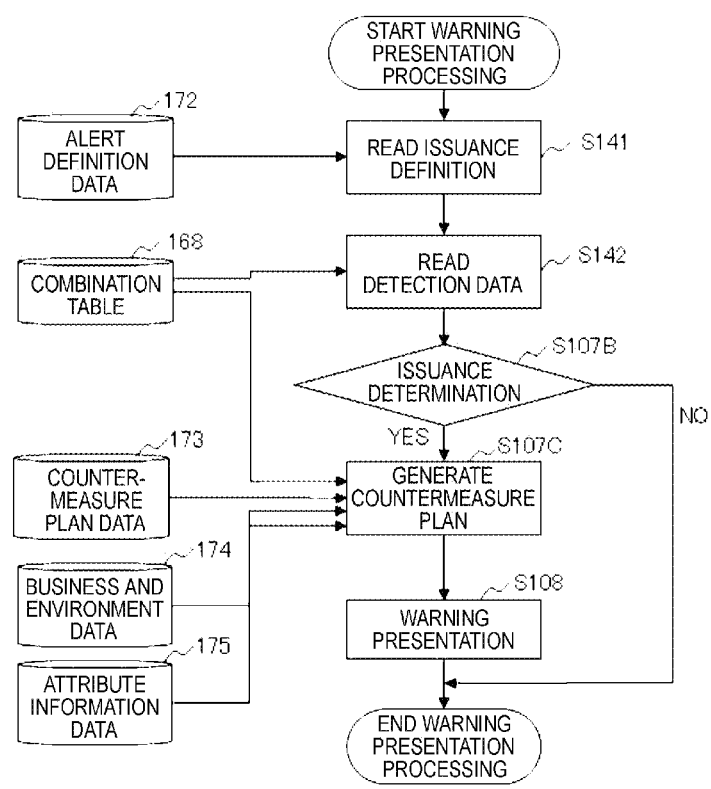

[FIG. 26A]
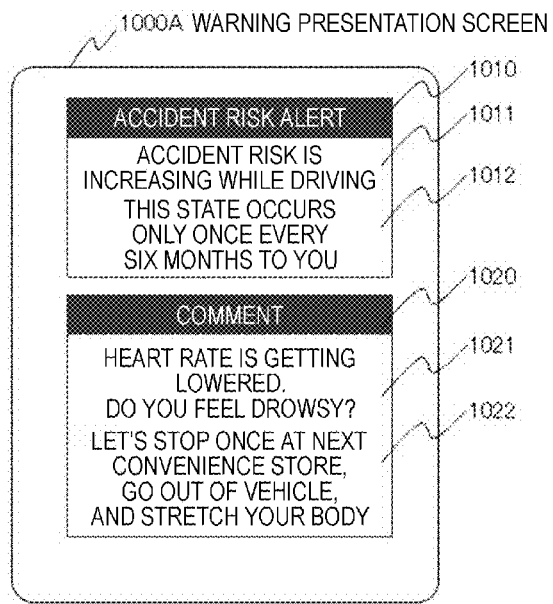
[FIG. 26B]
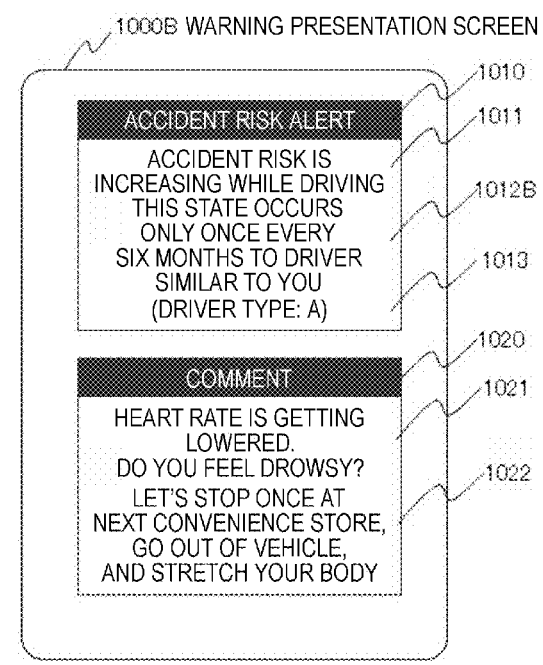

[FIG. 27A]

164 BIOLOGICAL INDEX DATA

| DRIVER ID /1401 | VEHICLE ID /1402 | DATE AND TIME /1403 | LF/HF /1404 | AVERAGE HEART RATE /1405 | NN50 /1406 | ... | α1 /1407 |
|---|---|---|---|---|---|---|---|
| ZAX001 | 01AB | 2020/04/01 10:00:00 | 1.2 | 80 | 0 | ... | 0.81 |
| ZAX001 | 01AB | 2020/04/01 10:30:00 | 0.9 | 60 | 3 | ... | 0.82 |
| ... | ... | ... | ... | ... | ... | ... | ... |

[FIG. 27B]

174 BUSINESS AND ENVIRONMENT DATA

| DRIVER ID /411 | START DATE AND TIME /412 | END DATE AND TIME /413 | VEHICLE ID /414 | VEHICLE TYPE /415 | WEATHER /416 | TEMPERA -TURE /417 | ... | BUSINESS TYPE /418 | BUSINESS SCHEDULE /419 |
|---|---|---|---|---|---|---|---|---|---|
| ZAX001 | 2020/04/01 08:35:00 | 2020/04/01 12:10:00 | 01AB | 2t | GOOD WEATHER | 10 | ... | DRIVING | XX:YY A FACTORY |
| ZAX001 | 2019/04/01 12:10:00 | 2020/04/01 12:40:00 | 01AB | 2t | GOOD WEATHER | 15 | ... | RESTING | ~ |
| ... | ... | ... | ... | ... | ... | ... | ... | ... | ... |

[FIG. 27C]

175 ATTRIBUTE INFORMATION DATA

| DRIVER ID | START DATE | END DATE | VEHICLE ID | SKILL A | PERSONALITY A | GENDER | AGE | DRIVING EXPERIENCE | BIOLOGICAL STATE ESTIMATION MODEL ID | ACCIDENT RISK PREDICTION MODEL ID |
|---|---|---|---|---|---|---|---|---|---|---|
| ZAX001 | 2019/01/21 | - | 01AB | 60 | A | MAN | 25 | 3 | 〇-〇-202004-M1 | 〇-〇-2020Q1 |
| ZAX002 | 1999/10/01 | - | 01AC | 90 | B | MAN | 55 | 25 | 〇-〇-202004-18 | 〇-〇-2020Q1 |
| ... | ... | ... | ... | ... | ... | ... | ... | ... | ... | ... |

[FIG. 27D]

176 LEARNING INFORMATION DATA

| DRIVER ID | START TIME | END TIME | MEASUREMENT CONDITIONS | VAS |
|---|---|---|---|---|
| ZAX001 | 2020/04/01 10:00:00 | 2020/04/01 11:00:00 | HIGH-SPEED DRIVING | — |
| ZAX002 | 2020/04/01 12:30:00 | 2020/04/01 13:00:00 | LUNCH BREAK | 60 |
| ... | ... | ... | ... | ... |

162 HAZARD OCCURRENCE DATA

| VEHICLE ID | DATE AND TIME | HAZARD TYPE | IMPORTANCE LEVEL |
|---|---|---|---|
| 01AC | 2020/02/23 14:33:12 | LACK OF DISTANCE BETWEEN VEHICLES | 80 |
| 01AC | 2020/02/25 15:27:48 | WOBBLY | 75 |
| ... | ... | ... | ... |

166 ACCIDENT RISK PREDICTION DATA

| DRIVER ID | DATE AND TIME | ACCIDENT RISK PREDICTION MODEL ID | ACCIDENT RISK |
|---|---|---|---|
| ZAX001 | 2020/04/01 10:00:00 | Risk-A-2020Q1 | 90 |
| ZAX001 | 2020/04/02 10:50:00 | Risk-A-2020Q1 | 85 |
| ... | ... | ... | ... |

167 PERSON'S SEVERITY LEVEL DATA

| DRIVER ID | DATE AND TIME | BIOLOGICAL DATA TYPE | BIOLOGICAL STATE ESTIMATION MODEL ID | PERSON'S SEVERITY LEVEL |
|---|---|---|---|---|
| ZAX001 | 2020/04/01 10:00:00 | AVERAGE HEART RATE | Stat-AVGHR-202004-M1 | +4SD |
| ZAX001 | 2020/04/02 10:50:00 | NN50 | Quantile-NN50-202004-M1 | 99 |
| ... | ... | ... | ... | ... |

168 COMBINATION TABLE

| DRIVER ID | VEHICLE ID | DATE AND TIME | ACCIDENT RISK PREDICTION MODEL ID | ACCIDENT RISK | CONTRIBUTION INDEX | BIOLOGICAL STATE ESTIMATION MODEL ID | PERSON'S SEVERITY LEVEL | ISSUED FLAG |
|---|---|---|---|---|---|---|---|---|
| ZAX001 | 01AB | 2020/04/01 10:00:00 | Risk-A-2020Q1 | 90 | AVERAGE HEART RATE | Stat-AVGHR-202004-M1 | 99 | COMPLETED |
| ZAX001 | 01AB | 2020/04/02 10:50:00 | Risk-A-2020Q1 | 85 | NN50 | Quantile-NN50-202004-M1 | +4SD | COMPLETED |
| ... | ... | ... | ... | ... | ... | ... | ... | ... |

[FIG. 27I]

172 ALERT DEFINITION DATA

| ALERT ID (1491) | ACCIDENT RISK THRESHOLD VALUE (1492) | PERSON'S SEVERITY LEVEL THRESHOLD VALUE (1493) | CONTRIBUTION INDEX CONDITION (1494) | WEATHER CONDITION (1495) | PERSON'S SEVERITY LEVEL TYPE (1496) | ... |
|---|---|---|---|---|---|---|
| 1 | >90 | >90 | – | – | Quantile | ... |
| 2 | >75 | >95 | – | – | Quantile | ... |
| ... | ... | ... | ... | ... | ... | ... |

[FIG. 27J]

173 COUNTERMEASURE PLAN DATA

| PLAN ID (1501) | CONTRIBUTION INDEX (1502) | PHENOMENON (1503) | INTERPRETATION (1504) | COUNTERMEASURE PLAN (1505) | PRIORITY (1506) | ... |
|---|---|---|---|---|---|---|
| 1 | AVERAGE HEART RATE | DECREASE | INCREASED DROWSINESS | LET'S STOP ONCE AT NEXT CONVENIENCE STORE, GO OUT OF VEHICLE, AND STRETCH YOUR BODY | 1 | ... |
| 2 | LF/HF | INCREASE | OVERSTRAIN | IF YOU DEEPLY BREATHE, YOU WILL FEEL CALM | 1 | ... |
| ... | ... | ... | ... | ... | ... | ... |

[FIG. 28]
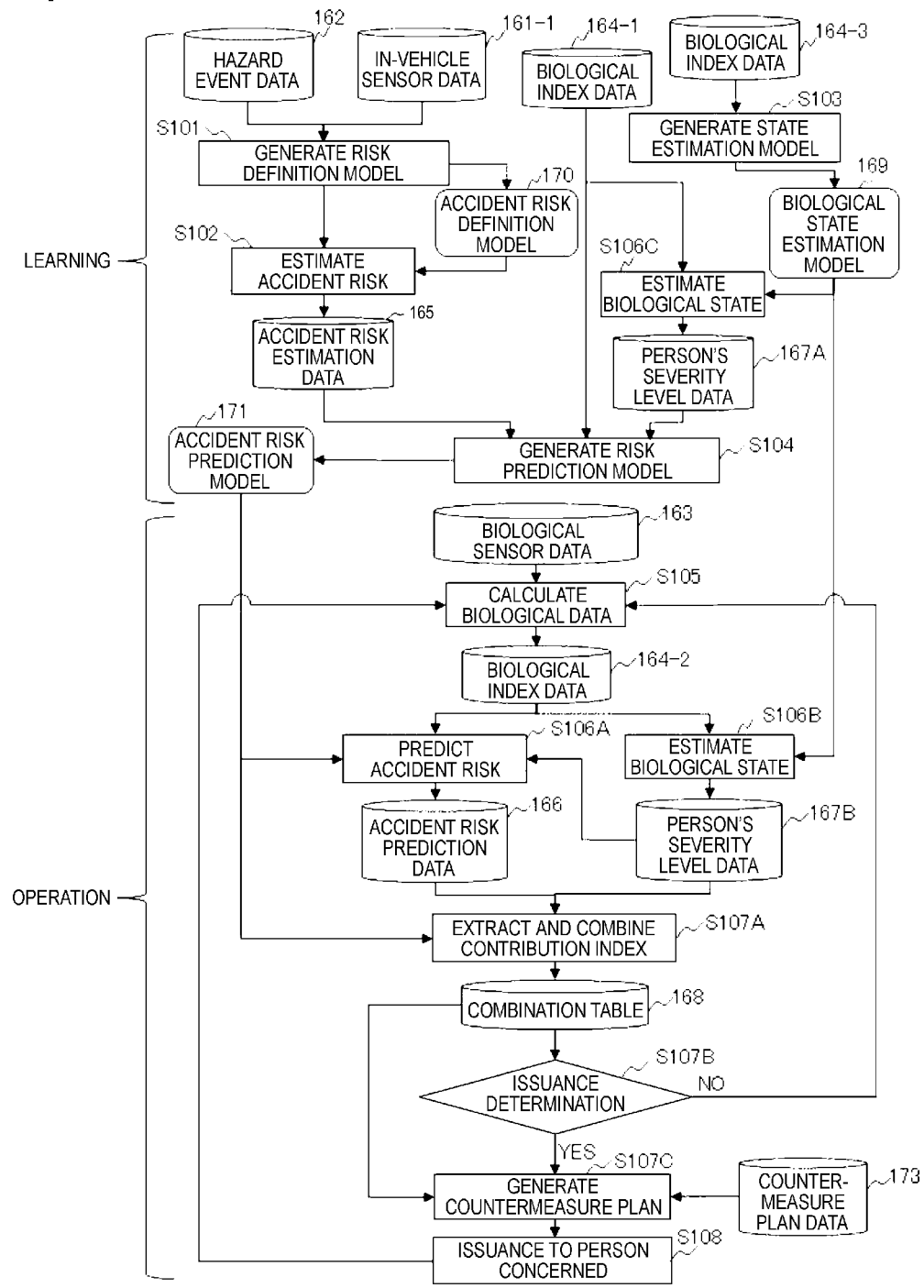

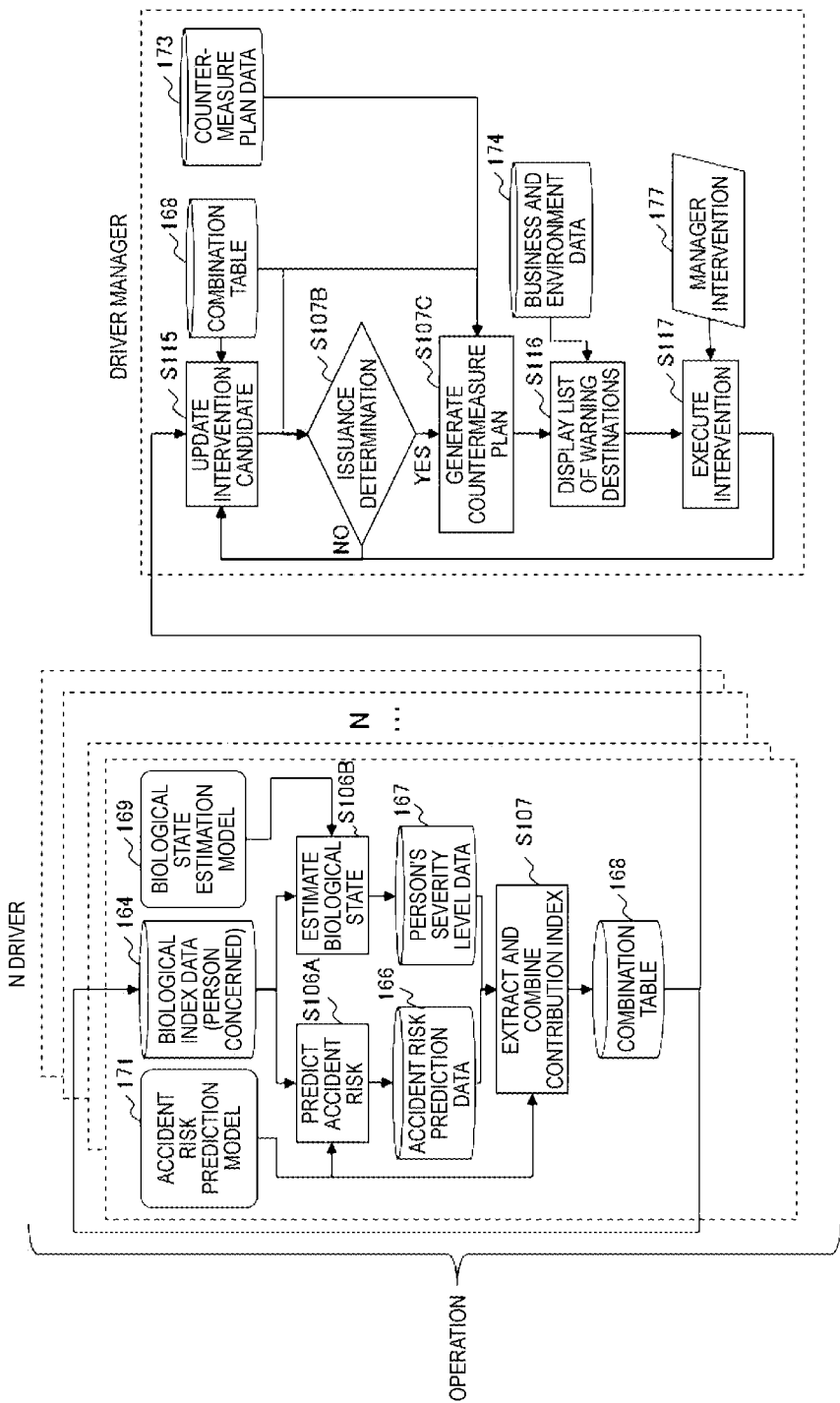
[FIG. 29]

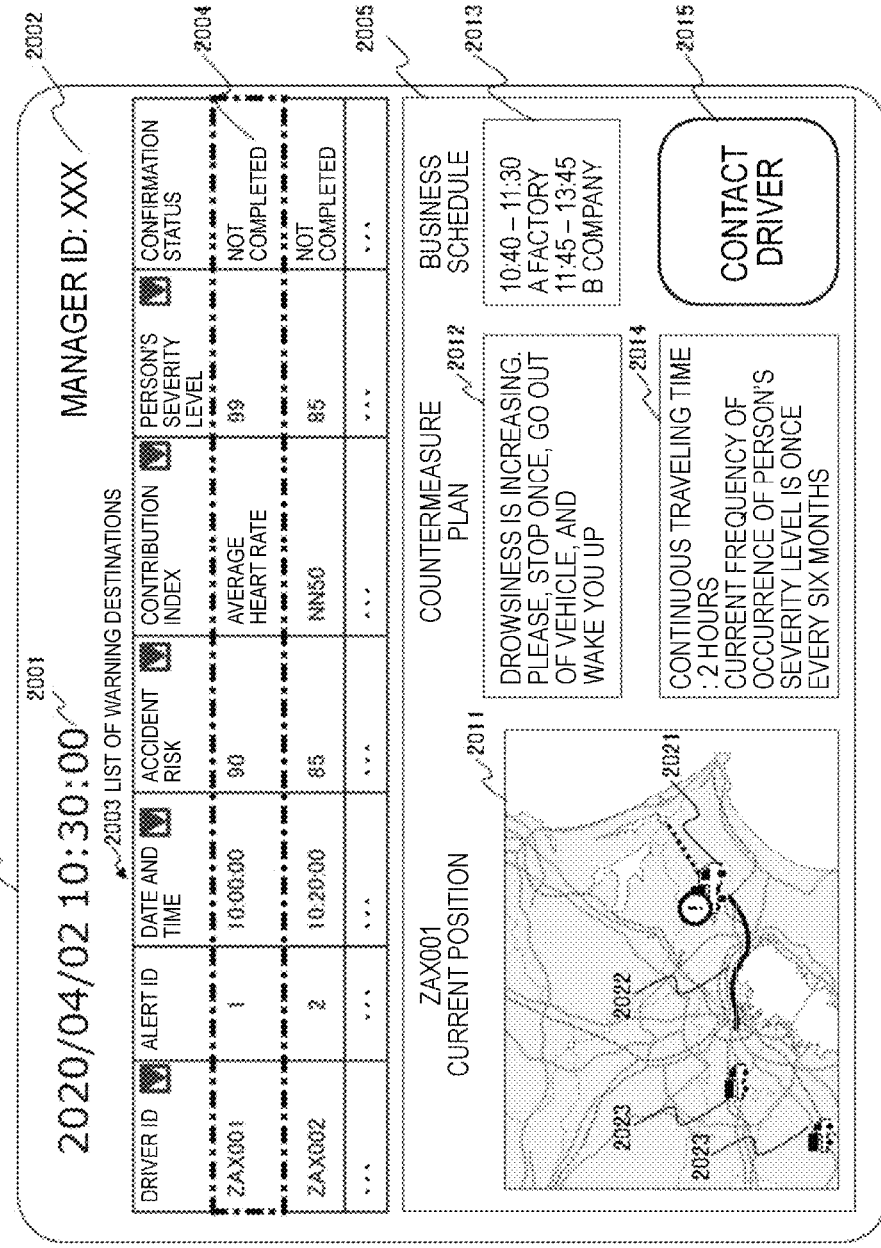
[FIG. 30]

OPERATION SUPPORT METHOD, OPERATION SUPPORT SYSTEM, AND OPERATION SUPPORT SERVER

This application claims the benefit of priority from Japanese Patent Application No. 2020-100060, filed on Jun. 9, 2020, and Japanese Patent Application No. 2020-157573, filed on Sep. 18, 2020, the entire contents of which are incorporated herein by reference.

TECHNICAL FIELD

The present invention relates to an operation support method, an operation support system, and an operation support server, configured to predict the risk of a traffic accident and to support the operation of a transportation facility.

BACKGROUND ART

In recent years, occurrence of a traffic accident caused by the health state and fatigue of a driver has become a social problem in a logistics truck and a long-distance bus. In order to prevent a traffic accident, the application of a biological sensor configured to monitor the state of a driver who is driving a vehicle and a technique of measuring a driving state of a vehicle such as a distance between vehicles and a speed in real time is progressing.

As a technique of supporting a vehicle driving operation, there are disclosed in JP-A-2009-245147 (PTL 1) and JP-A-2009-098970 (PTL 2). PTL 1 discloses a technique configured to update a table including a causal relationship with physiological state data unrelated to a driving operation and a driving status as well as a causal relationship between driving status data and driving operation data, to predict a driving operation related to sudden braking including a tolerance, and to perform efficient and accurate driving support.

PTL 2 discloses a technique configured to recognize a deviation from a normal internal state of a driver by comparing a traveling environment risk included in an external environment recognized by sensing an external environment of a moving body with a driver's risk recognition state estimated as an internal state from a driver's driving operation.

CITATION LIST

Patent Literature

PTL 1: JP-A-2009-245147
PTL 2: JP-A-2009-098970

SUMMARY OF INVENTION

Technical Problem

Meanwhile, in related art, it is possible to predict a driving operation of sudden braking based on physiological state data of a driver, driving operation data, and driving status data, but the prediction in related art focuses on a specific driving operation. Accordingly, there is a problem in that it is difficult to predict an event that does not occur frequently, such as a traffic accident.

Therefore, the present invention has been made in view of the above-described problems, and it is an object of the present invention to provide a operation support method, an operation support system, and an operation support server capable of predicting the risk of a traffic accident based on biological data of a driver and traveling state data.

Solution to Problem

The present invention provides an operation support method configured to support operation of a vehicle by a computer including a processor and a memory, the method including: a first step of inputting first in-vehicle sensor data indicating a traveling state of the vehicle, the first in-vehicle sensor data being collected in the past, and hazard occurrence data having information on hazard occurrence from the first in-vehicle sensor data preset therein, and generating an accident risk definition model configured to estimate a probability of the hazard occurrence by machine learning as an accident risk; a second step of inputting second in-vehicle sensor data indicating the traveling state of the vehicle, the second in-vehicle sensor data being collected in the past, to the accident risk definition model, and generating accident risk estimation data by estimating the probability of the hazard occurrence; a third step of inputting first biological index data and the accident risk estimation data, wherein the first biological index data is calculated in advance from biological data of a driver when the second in-vehicle sensor data is collected, and generating an accident risk prediction model by machine learning, wherein the accident risk prediction model predicts an accident risk after a predetermined time; a fourth step of acquiring biological data of a driver who is driving the vehicle, and calculating, second biological index data indicating a state of the driver from the biological data; and a fifth step of inputting the second biological index data to the accident risk prediction model, and predicting the accident risk after the predetermined time.

Advantageous Effects of Invention

Therefore, according to the present invention, it is possible to predict the risk of occurrence of an event such as a traffic accident after a predetermined time based on biological data of a driver and traveling state data.

Details of the implementation of at least one of the subject matters disclosed in this specification are set forth in the accompanying drawings and in the following descriptions. Other features, aspects, and effects of the subject matters to be disclosed herein are revealed by the following disclosures, drawings, and claims.

BRIEF DESCRIPTION OF DRAWINGS

FIG. 1 shows a first embodiment of the present invention, and is a block diagram showing an example of a configuration of an operation support system.

FIG. 2 shows the first embodiment of the present invention, and is a diagram showing an outline of processing performed by the operation support system.

FIG. 3 shows the first embodiment of the present invention, and is a flowchart showing an example of generation processing of an accident risk prediction model performed by an operation support server.

FIG. 4 shows the first embodiment of the present invention, and is a flowchart showing an example of generation processing of biological index data performed by the operation support server.

FIG. 5 shows the first embodiment of the present invention, and is a flowchart showing an example of prediction processing performed by the operation support server.

FIG. 6 shows the first embodiment of the present invention, and is a flowchart showing an example of alert generation processing performed by the operation support server.

FIG. 7A shows the first embodiment of the present invention, and is a flowchart showing an example of calculation processing of a biological index performed by the operation support server.

FIG. 7B shows the first embodiment of the present invention, and is a graph showing an example of heart rate data.

FIG. 7C shows the first embodiment of the present invention, and is a graph showing an example of heart rate variability.

FIG. 7D shows the first embodiment of the present invention, and is a graph showing an example of spectral power density of the heart rate variability.

FIG. 7E shows the first embodiment of the present invention, and is a graph showing an example of an autonomic nerve NNXX.

FIG. 8 shows the first embodiment of the present invention, and is a diagram showing an example of biological index data.

FIG. 9 shows the first embodiment of the present invention, and is a diagram showing an example of business data.

FIG. 10 shows the first embodiment of the present invention, and is a diagram showing an example of environmental data.

FIG. 11 shows the first embodiment of the present invention, and is a diagram showing an example of in-vehicle sensor data.

FIG. 12 shows the first embodiment of the present invention, and is a diagram showing an example of hazard occurrence data.

FIG. 13 shows the first embodiment of the present invention, and is a diagram showing an example of accident risk estimation data.

FIG. 14 shows the first embodiment of the present invention, and is a diagram showing an example of alert definition data.

FIG. 15 shows the first embodiment of the present invention, and is a diagram showing an example of accident risk prediction data.

FIG. 16A shows the first embodiment of the present invention, and is a diagram showing an example of a prediction result display screen.

FIG. 16B shows the first embodiment of the present invention, and is a diagram showing an example of a prediction result notification screen.

FIG. 17 shows a second embodiment of the present invention, and is a block diagram showing an example of a configuration of an operation support system.

FIG. 18 shows a third embodiment of the present invention, and is a block diagram showing an example of a configuration of an operation support system.

FIG. 19 shows the third embodiment of the present invention, and is a diagram showing an outline of processing performed by the operation support system.

FIG. 20 shows the third embodiment of the present invention, and is a flowchart showing an example of generation processing of an accident risk prediction model performed by an operation support server.

FIG. 21 shows a fourth embodiment of the present invention, and is a flowchart showing an example of generation processing of a biological state estimation model performed by an operation support server.

FIG. 22 shows the third embodiment of the present invention, and is a flowchart showing an example of calculation processing of biological data performed by the operation support server.

FIG. 23 shows the third embodiment of the present invention, and is a flowchart showing an example of calculation processing of biological data using heart rate data performed by the operation support server.

FIG. 24 shows the third embodiment of the present invention, and is a flowchart showing an example of hazard prediction processing performed by the operation support server.

FIG. 25 shows the third embodiment of the present invention, and is a flowchart showing an example of warning presentation processing performed by the operation support server.

FIG. 26A shows the third embodiment of the present invention, and is a diagram showing an example of a warning presentation screen.

FIG. 26B shows the third embodiment of the present invention, and is a diagram showing another example of the warning presentation screen.

FIG. 27A shows the third embodiment of the present invention, and is a diagram showing an example of a data structure of the biological data.

FIG. 27B shows the third embodiment of the present invention, and is a diagram showing an example of a data structure of business and environment data.

FIG. 27C shows the third embodiment of the present invention, and is a diagram showing an example of a data structure of attribute information data.

FIG. 27D shows the third embodiment of the present invention, and is a diagram showing an example of a data structure of learning information data.

FIG. 27E shows the third embodiment of the present invention, and is a diagram showing an example of a data structure of hazard occurrence data.

FIG. 27F shows the third embodiment of the present invention, and is a diagram showing an example of a data structure of accident risk prediction data.

FIG. 27G shows the third embodiment of the present invention, and is a diagram showing an example of a data structure of person's severity level data.

FIG. 27H shows the third embodiment of the present invention, and is a diagram showing an example of a data structure of a combination table.

FIG. 27I shows the third embodiment of the present invention, and is a diagram showing an example of a data structure of alert definition data.

FIG. 27J shows the third embodiment of the present invention, and is a diagram showing an example of a data structure of countermeasure plan data.

FIG. 28 shows the fourth embodiment of the present invention, and is a diagram showing an outline of processing performed by an operation support system.

FIG. 29 shows a fifth embodiment of the present invention, and is a diagram showing an outline of processing performed by an operation support system.

FIG. 30 shows the fifth embodiment of the present invention, and is a diagram showing an example of a warning destination list screen provided to a driver manager.

DESCRIPTION OF EMBODIMENTS

Hereinafter, embodiments of the present invention will be described based on the attached drawings.

First Embodiment

FIG. 1 shows a first embodiment of the present invention, and is a block diagram showing an example of a configuration of an operation support system.

The operation support system of the embodiment includes an operation support server 1 configured to support operation of one or more vehicles 7 via a network 13. The vehicle 7 includes an in-vehicle sensor 8 configured to detect a traveling state, a biological sensor 12 configured to detect biological data of a driver, a driver ID reader 11 configured to specify a driver, a driving data collection device 10 configured to collect detected sensor data and a driver ID and to transmit the same to the operation support server 1, and a prediction result notification device 9 configured to receive, from the operation support server 1, a notification in accordance with a driver's traffic accident risk (hereinafter referred to as an accident risk) and to notify the driver of the notification.

In the example shown in the drawing, the driving data collection device 10 and the prediction result notification device 9 are independent devices, but the same can be formed as one portable terminal. In this case, the portable terminal functions as a driving data collection unit and a prediction result notification unit.

The in-vehicle sensor 8 can include a global navigation satellite system (GNSS) 81 configured to detect position information of the vehicle 7, an acceleration sensor 82 configured to detect the behavior and speed of the vehicle 7, and a camera 83 configured to detect a traveling environment as an image.

The in-vehicle sensor 8 is not limited thereto, but a ranging sensor configured to detect an object around the vehicle 7 and a distance thereof, a steering angle sensor configured to detect a driving operation, and the like can be used. The acceleration sensor 82 is preferably a triaxial acceleration sensor.

The biological sensor 12 includes a heart rate sensor 121 configured to detect heart rate data and an acceleration sensor 122 configured to detect movement of a driver. The biological sensor 12 is not limited thereto, but a sensor configured to detect the amount of sweating, body temperature, blinking, eye movement, brain waves, or the like can be adopted. As the biological sensor 12, in addition to a wearable device that can be worn by a driver, it is possible to use a sensing device attached to the inside of the vehicle 7 such as a steering wheel, a seat, and a seat belt, and an image recognition system configured to capture the facial expression and behavior of a driver and to analyze a captured image thereof.

The driver ID reader 11 reads a card in which a driver identifier is recorded. The driving data collection device 10 collects data from the in-vehicle sensor 8 and the biological sensor 12 at a predetermined cycle, and transmits the collected data to the operation support server 1 via the network 13.

The operation support server 1 is a computer including a processor 2, a memory 3, a storage device 4, an input and output device 5, and a communication device 6. The memory 3 loads, as a program, each functional unit of a biological index calculation unit 31, an accident risk definition generation unit 32, an accident risk prediction model generation unit 33, a prediction model selection unit 34, an accident risk prediction unit 35, an accident risk notification unit 36, and a data collection unit 37. Each program is executed by the processor 2. Details of each functional unit will be described later.

The processor 2 operates as a functional unit configured to provide a predetermined function by executing processing according to a program of each functional unit. For example, the processor 2 functions as the biological index calculation unit 31 by executing a biological index calculation program. The same is true for other programs. Furthermore, the processor 2 also operates as a functional unit configured to provide respective functions of a plurality of pieces of processing executed by respective programs. A computer and a computer system are a device and a system including these functional units.

The storage device 4 stores data used by each functional unit. The storage device 4 stores in-vehicle sensor data 40, biological sensor data 41, business data 42, an accident risk prediction model 43, accident risk prediction data 44, hazard occurrence data 45, biological index data 46, environmental data 47, an accident risk definition model 48, alert definition data 49, and accident risk estimation data 50. Details of each piece of data will be described later.

The input and output device 5 includes an input device such as a mouse, a keyboard, or a touch panel, and an output device such as a display. The communication device 6 communicates with the vehicle 7 via the network 13.

<Outline of Operation Support System>

FIG. 2 is a diagram showing an outline of processing performed by the operation support system. First, the accident risk definition generation unit 32 inputs the preset hazard occurrence data 45 and in-vehicle sensor data 40-$m1$ collected in the past, thereby generating the accident risk definition model 48 configured to estimate the probability of the hazard occurrence as an accident risk (S1). The accident risk definition model 48 estimates the probability of the hazard occurrence by inputting in-vehicle sensor data 40-$m2$ indicating a traveling state of the vehicle 7.

The hazard occurrence data 45 is data in which a manager or the like determines an incident or an event leading to an incident from the time-series in-vehicle sensor data 40-$m1$ indicating the traveling state of the vehicle 7, and sets a date and time of occurrence and an importance level of the incident.

For example, when the in-vehicle sensor data 40-$m1$ is the sensor data of the acceleration sensor 82, an incident such as sudden braking and sudden turning or a traveling state leading to an incident is detected, and a manager or the like sets an importance level of hazard occurrence to generate the hazard occurrence data 45.

In addition, an importance level shows an example in which the risk increases as a value of the importance level increases. Further, the traveling state leading to the incident indicates a state in which a driver becomes nervous (or startled). In the following descriptions, an incident or a traveling state leading to an incident is regarded as hazard occurrence.

In the generation of the hazard occurrence data 45, the operation support server 1 detects a traveling state in which a forward-and-rearward acceleration exceeds a predetermined threshold value or a traveling state (hazard occurrence) in which a yaw rate exceeds a predetermined threshold value, and a manager or the like may set an importance level of an event of the detected hazard occurrence.

The time series of the in-vehicle sensor data 40-$m1$ shown in FIG. 2 and the time series of the hazard occurrence data 45 are the same time series.

The accident risk definition generation unit 32 inputs the in-vehicle sensor data 40-$m1$ and the hazard occurrence data 45, and generates a machine learning model configured to estimate an accident risk from a traveling state as the accident risk definition model 48.

Since a well-known or known method such as a neural network and logistic regression may be adopted as a machine learning model, the machine learning model is not described in detail in the embodiment. Further, an accident risk is the probability (percentage) of causing an incident (or hazard occurrence). Additionally, in the embodiment, an event leading to a traffic accident is regarded as an incident.

Next, the accident risk definition generation unit 32 inputs, to the generated accident risk definition model 48, the in-vehicle sensor data 40-$m2$ collected in the past, which is a time series different from the in-vehicle sensor data 40-$m1$, and outputs a probability of occurrence of an accident risk to generate the accident risk estimation data 50 (S2).

The accident risk estimation data 50 is data in which the probability that an incident occurs (or the probability that an accident occurs) with respect to the in-vehicle sensor data 40-$m2$ is generated in the same time series as the in-vehicle sensor data 40-$m2$.

Next, the biological index calculation unit 31 calculates biological index data 46-$m$ of a driver from the past biological sensor data 41 (biological data of a driver), corresponding to when the in-vehicle sensor data 40-$m2$ is acquired. As the biological index data 46-$m$, for example, it is possible to use an autonomic nervous index or the like (described later) based on power spectral density (described later) calculated from heart rate data of a driver and an NN interval (an interval between an R wave and an R wave) calculated from time-domain analysis.

The in-vehicle sensor data 40-$m1$ and 40-$m2$ collected in the past and the biological index data 46-$m$ may be stored in a predetermined area of the storage device 4.

Next, the accident risk prediction model generation unit 33 inputs the accident risk estimation data 50 and the biological index data 46-$m$, and generates, as the accident risk prediction model 43, a machine learning model configured to output an accident risk (a probability) after a predetermined time from the biological index data 46 of the traveling vehicle 7 (S3).

The accident risk prediction model 43 may generate a plurality of models according to a type of in-vehicle sensor data 40 to be used and the environment in which prediction is performed, and the prediction model selection unit 34 may select a model to be used.

Further, the accident risk prediction model 43 may generate a plurality of types of models according to a type in accordance with a difference in driving characteristics of the vehicle 7, driving history of a driver, biological data before operation, and the like. For example, as a difference in driving characteristics of the vehicle 7, it is desirable to generate a different model for a vehicle model having a different steering wheel operation during turning or reversing, such as a truck and a trailer. Further, as the driving history of a driver, it is desirable to generate a model based on differences in accuracy of driving operation, hazard sensitivity, number of years of driving experience, a driving experience vehicle (a large size, a special size, and the like), traveling route history, and the like. Additionally, as the biological data before operation of a driver, it is desirable to generate a model based on differences in body temperature, blood pressure, blood oxygen concentration, sleeping hours on the previous day, and the like.

Next, the operation support server 1 predicts the accident risk of the vehicle 7 actually traveling by using the generated accident risk prediction model 43 (S4). In the operation support server 1, when a plurality of accident risk prediction models 43 are provided, the prediction model selection unit 34 selects the accident risk prediction model 43 in accordance with the in-vehicle sensor data 40 to be used, the environmental data 47 of the vehicle 7, and the like.

The accident risk prediction unit 35 inputs, to the biological index calculation unit 31, the heart rate data of the biological sensor 12 received by the data collection unit 37 via the vehicle 7, thereby calculating the biological index data 46. The accident risk prediction unit 35 inputs the calculated biological index data 46 to the accident risk prediction model 43, thereby predicting an accident risk in the future from the present until after a predetermined time $\Delta t$. When the accident risk prediction model 43 outputs interpretation data (described later) indicating the state of a driver, the accident risk prediction unit 35 can add the interpretation data to a predicted value of the accident risk.

When the accident risk after the predetermined time $\Delta t$ is equal to or greater than a predetermined threshold value Th, the accident risk notification unit 36 generates an alert and a message according to a value of the accident risk, the interpretation data, the driving state, or the environmental data, and transmits the alert and the message to the vehicle 7 having an accident risk predicted to increase (S5).

When the vehicle 7 receives the alert from the operation support server 1, the prediction result notification device 9 outputs the alert, and transmits the alert or the message to the driver. In addition, when the accident risk is predicted to increase after the predetermined time $\Delta t$, the accident risk notification unit 36 can generate an image including position information of the corresponding vehicle 7, an accident risk and an amount of work of a driver, and the like for a manager or the like of the operation support server 1, and can display the generated image on the display of the input and output device 5.

The operation support server 1 predicts that the accident risk will be equal to or greater than the threshold value Th after the predetermined time $\Delta t$, and notifies the prediction result notification device 9 of the corresponding vehicle 7 and the display of the input and output device 5 of the prediction, thereby making it possible to cause a driver and a manager to be careful of an accident risk with an alert and a message before the accident risk increases. Accordingly, the operation support server 1 can reduce actual accident risk 51 and promote the safe operation of each vehicle 7.

In addition, it is desirable to set the predetermined time $\Delta t$ of predicting the accident risk in the future to a value such as 30 minutes or 1 hour, and therefore, it is possible to advise a driver to take a break or give advice to a driver before the time when the accident risk increases.

<Data>

Next, each piece of data used in the operation support system will be described.

FIG. 8 is a diagram showing an example of the biological index data 46. The biological index data 46 is a table configured to store data calculated by the biological index calculation unit 31 for each predetermined period from the heart rate data of the biological sensor data 41.

The biological index data 46 includes, in one record, a user ID 460, a date and time 461, an autonomic nerve total power 462, an autonomic nerve LF/HF 463, an autonomic nerve NN50 465, and an average RRI 464. A driver identifier is stored in the user ID 460. The date and time when the biological sensor data 41 (the heart rate data) are acquired is stored in the date and time 461.

As described later, in the autonomic nerve total power 462, a total value of a low-frequency (LF) component and a high-frequency (HF) component of power spectral density of an R-wave interval (RRI) of the heart rate data is stored as a value indicating the balance of autonomic nerves (sympathetic nerves and parasympathetic nerves).

The autonomic nerve LF/HF 463 stores a ratio of the low-frequency (LF) component to the high-frequency (HF) component of the power spectral density. The low-frequency component indicates an activity index of the sympathetic nerve, and the high-frequency component indicates an activity index of the parasympathetic nerve. The average RRI 464 stores an average value of the R-wave interval (RRI) within a preset period.

In the autonomic nerve NN50 465, as described later, the total number of difference values is stored as a value indicating the magnitude of parasympathetic nerve activity. Here, the difference values are equal to or greater than 50 msecs with respect to a difference series ΔRRI(t) of the heart rate variability time-series data RRI.

The illustrated example shows an example of calculating the autonomic nerve total power 462, the autonomic nerve LF/HF 463, and the autonomic nerve NN50 465 at one-minute intervals, but the present invention is not limited thereto. The biological index data 46 may be calculated at an appropriately set time interval.

FIG. 9 is a diagram showing an example of the business data 42. The business data 42 is a table configured to store information on management of the vehicle 7 driven by a driver and business, and is set by a person in charge of the operation support system, a manager, and the like.

The business data 42 includes, in one record, a user ID 420, a business start date and time 421, a business end date and time 422, a vehicle ID 423 configured to store an identifier of the vehicle 7, and a business type 424. The business type 424 stores business contents of a driver.

FIG. 10 is a diagram showing an example of the environmental data 47. The environmental data 47 is a table configured to store information based on the in-vehicle sensor data 40 of the vehicle 7. The environmental data 47 stores a vehicle ID 470 configured to store an identifier of the vehicle 7, a date and time 471 when the environmental data 47 is generated, a traffic jam status 472 of the road on which the vehicle 7 travels, weather 473, and temperature 474.

The traffic jam status 472 may be determined from an image of the camera 83 of the vehicle 7, or may be acquired from a traffic information service on the network 13 based on the position information calculated by the GNSS 81.

FIG. 11 is a diagram showing an example of the in-vehicle sensor data 40. The in-vehicle sensor data 40 is a table configured to store information collected by the data collection unit 37 from the in-vehicle sensor 8 of the vehicle 7 at a predetermined cycle.

The in-vehicle sensor data 40 includes, in one record, a vehicle ID 400 configured to store an identifier of the vehicle 7, a date and time 401 when data is acquired from the in-vehicle sensor 8, a position 402 configured to store position information detected by the GNSS 81, a speed 403 of the vehicle 7, and an acceleration 404 detected by the acceleration sensor 82.

FIG. 12 is a diagram showing an example of the hazard occurrence data 45. The hazard occurrence data 45 is a table generated based on the in-vehicle sensor data 40-$m1$, as shown in FIG. 2.

The hazard occurrence data 45 includes, in one record, a vehicle ID 450 configured to store an identifier of the vehicle 7, a date and time 451 of hazard occurrence, a hazard type 452 configured to store a type of the occurred hazard, and an importance level 453 of the occurred hazard. A value determined by a manager or the like is stored in the hazard type 452 and the importance level 453.

In the hazard occurrence data 45, a manager or the like determines an incident or a state causing an incident from the traveling state of the vehicle 7 indicated by the in-vehicle sensor data 40-$m1$, and sets the hazard type 452 and the importance level 453.

FIG. 13 is a diagram showing an example of the accident risk estimation data 50. The accident risk estimation data 50 is a table in which the accident risk definition generation unit 32 inputs the in-vehicle sensor data 40-$m2$ to the accident risk definition model 48 to estimate an accident risk.

The accident risk estimation data 50 includes, in one record, a user ID 500 configured to store a driver identifier, a vehicle ID 501 configured to store an identifier of the vehicle 7, a date and time 502 when an accident risk occurs, and an accident risk 503 configured to store the probability (percentage) leading to an incident.

The accident risk 503 is a result obtained by providing the speed, acceleration, and position information of the vehicle 7 to the accident risk definition model 48 and estimating a probability of occurrence of an incident. In the illustrated example, an example of calculating the accident risk 503 at one-minute intervals is shown, but the present invention is not limited thereto.

FIG. 14 is a diagram showing an example of the alert definition data 49. The alert definition data 49 is a table in which an alert or a message to be notified by the accident risk notification unit 36 is set in advance.

The alert definition data 49 includes, in one record, an alert ID 490, an accident risk condition 491, a time condition 492, a traffic jam condition 493, a weather condition 494, a priority 495, and a comment 496.

The alert ID 490 stores an identifier configured to specify an alert. The accident risk condition 491 stores an accident risk condition configured to select an alert of the record. For example, in the record of the alert ID 490="1", a condition to be selected when a value of the accident risk is 70% or less is set.

In the time condition 492, a time zone is set to select an alert of the record. In the traffic jam condition 493, a traffic jam status (no traffic jam or occurrence of traffic jam) is set to select an alert of the record. In the weather condition 494, weather is set to select an alert of the record.

In the priority 495, when a plurality of records satisfying the accident risk condition 491 are extracted, the priority of the record to be selected is set in advance. The comment 496 stores contents of an alert (or a message) to be notified.

FIG. 15 is a diagram showing an example of the accident risk prediction data 44. The accident risk prediction data 44 is a table configured to store a prediction result of an accident risk calculated by the accident risk prediction model 43 having the biological sensor data 41 of a driver of the traveling vehicle 7 inputted thereto.

The accident risk prediction data 44 includes, in one record, a user ID 440, a vehicle ID 441, a date and time 442 when the in-vehicle sensor data 40 is acquired, a predicted date and time 443, and an accident risk 444.

The predicted date and time 443 stores the date and time after a predetermined time Δt. The accident risk 444 stores a predicted value (percentage) of the accident risk after the predetermined time Δt.

<Details of Processing>

Next, processing performed by the operation support system will be described.

FIG. 3 is a flowchart showing an example of generation processing of the accident risk prediction model 43 performed by the operation support server 1. This processing is performed before receiving the data of the in-vehicle sensor 8 and the biological sensor 12 are received from the vehicle 7 to generate the accident risk prediction model 43.

The accident risk definition generation unit 32 inputs the hazard occurrence data 45 generated in advance and the in-vehicle sensor data 40 (40-*m*1 in FIG. 2) collected in the past to generate the accident risk definition model 48 by machine learning (S11).

The accident risk definition generation unit 32 inputs the in-vehicle sensor data 40 (40-*m*2 in FIG. 2) collected in the past to the generated accident risk definition model 48, thereby generating the accident risk estimation data 50 (S12).

Next, the accident risk prediction model generation unit 33 acquires the biological index data 46-*m* corresponding to the in-vehicle sensor data 40 (40-*m*2 in FIG. 2) collected in the past, and generates the accident risk prediction model 43 from the accident risk estimation data 50 and the biological index data 46-*m* by machine learning (S13).

When performing the machine learning, the accident risk prediction model generation unit 33 acquires driver information from the business data 42, acquires a traveling environment of the vehicle 7 from the environmental data 47, and generates the accident risk prediction model 43.

After the accident risk definition model 48 is generated and the accident risk estimation data 50 is generated by the above-described processing, the accident risk prediction model 43 is generated from the biological index data 46 and the accident risk estimation data 50 collected in the past.

FIG. 4 is a flowchart showing an example of generation processing of the biological index data 46 performed by the operation support server 1. This processing is executed every time data is received from the vehicle 7. The data collection unit 37 of the operation support server 1 receives the data of the in-vehicle sensor 8 and the biological sensor 12 from the driving data collection device 10 of the vehicle 7 (S21).

The data collection unit 37 stores heart rate data and acceleration data detected by the heart rate sensor 121 and the acceleration sensor 122 in the biological sensor data 41 (S22). The data collection unit 37 stores the data of the in-vehicle sensor 8 in the in-vehicle sensor data 40.

Next, the biological index calculation unit 31 reads the biological sensor data 41 and calculates a biological index as described later (S23). The biological index calculation unit 31 stores the calculated biological index in the biological index data 46 (S24).

FIG. 7A is a flowchart showing an example of calculation processing of the biological index performed by the biological index calculation unit 31. This processing is executed in step S23 of FIG. 4.

The biological index calculation unit 31 acquires heart rate data from the biological sensor data 41 (S51). The acquired heart rate data is data within a predetermined period from the latest heart rate data. Next, the biological index calculation unit 31 calculates an RR interval (RRI) from an R-wave interval provided in the heart rate data (S52).

FIG. 7B is a diagram showing an example of heart rate data detected by the biological sensor 12. The biological index calculation unit 31 detects a time interval between a peak of the R-wave and a peak of the next R-wave in the drawing as the RRI, calculates a predetermined number (or a predetermined period) of RRIs as heart rate variability time-series data, and further calculates an average value of the RRIs as the average RRI 464.

Next, the biological index calculation unit 31 calculates fluctuation from the calculated heart rate variability time-series data. FIG. 7C is a graph showing an example of the fluctuation (heart rate variability) of the heart rate data calculated by the biological index calculation unit 31. The RRI of the heart rate data is not constant and fluctuates due to autonomic nerve activity or the like.

The biological index calculation unit 31 performs frequency spectral analysis from the time-series heart rate variability data (S53), and then calculates power spectral density (PSD) (S54). A well-known method may be applied to calculate the power spectral density.

Next, the biological index calculation unit 31 calculates an intensity LF of a low-frequency component of the power spectral density and an intensity HF of a high-frequency component thereof. FIG. 7D is a graph showing an example of a frequency domain of the power spectral density of the heart rate variability.

As shown in FIG. 7D, the biological index calculation unit 31 calculates, as the autonomic nerve total power 462, a total value (LF+HF) of the intensity (integral value) LF in a low-frequency component region of the power spectrum (0.05 Hz to 0.15 Hz) and the intensity (integral value) HF in a high-frequency component region thereof (0.15 Hz to 0.40 Hz).

Further, the biological index calculation unit 31 calculates, as the autonomic nerve LF/HF 463, a ratio (LF/HF) of the intensity LF of the low-frequency component of the power spectrum to the intensity HF of the high-frequency component thereof.

By the above-described processing, the time-series heart rate variability data is calculated from the heart rate data of the biological sensor data 41, and the intensities (LF and HF) of the low-frequency component and the high-frequency component are calculated, thereby making it possible to obtain the autonomic nerve total power 462 and the autonomic nerve LF/HF 463.

Here, the high-frequency component appears in the heart rate variability when the parasympathetic nerve is activated (tense), and the low-frequency component appears in the heart rate variability when the sympathetic nerve is activated (tense) and when the parasympathetic nerve is activated (tense).

Since it is known that when the sympathetic nerve is activated, this indicates a stressed state, and when the parasympathetic nerve is activated, this indicates a relaxed state, it is possible to determine whether a driver is in a stressed state or a relaxed state from the intensity LF of the low-frequency component and the intensity HF of the high-frequency component.

Thereafter, the biological index calculation unit 31 calculates a time-domain index obtained from the time-domain analysis of the heart rate variability time-series data RRI (S55). FIG. 7E is a graph showing an example of calculating an autonomic nerve NNXX, which is one of the time-domain indexes, from the difference series ΔRRI(t) of the heart rate variability time-series data RRI.

As shown in FIG. 7E, the biological index calculation unit 31 calculates ΔRRI(t) which is a difference series obtained by taking the difference between adjacent RRIs with respect to the heart rate variability time-series data RRI, and calculates, from ΔRRI(t), the autonomic nerve NNXX which is the total number of difference values. Here, the difference values forming ΔRRI(t) are equal to or greater than XX msecs. Typically, as shown in FIG. 7E, when XX=50, the autonomic nerve NN50 465, which is the total number of difference values (=the total number of difference values existing in a lattice shaded area), is calculated. Here, the difference values forming ΔRRI(t) are equal to or greater than 50 msecs.

Here, since it is known that the autonomic nerve NN50 465 is similar to the intensity HF of the high-frequency component and is an index representing the magnitude of the parasympathetic nerve activity, it is possible to determine the magnitude of a relaxed state of a driver from the autonomic nerve NN50 465.

Here, NNXX is not limited to the definition described above. For example, instead of the total number of difference values, wherein the difference values forming ΔRRI(t) are equal to or greater than 50 msecs, absNN50, which is the total number of difference values (=the total number of difference values existing in a lattice shaded area and a diagonally shaded area), may be calculated. Here, an absolute value of the difference values forming ΔRRI(t) is equal to or greater than 50 msecs. Alternatively, pNN50, which is a normalized value obtained by dividing the autonomic nerve NN50 465 by the total number of difference values included in ΔRRI(t) (=total number of difference values existing in the lattice shaded area total number of difference values existing in a dotted shaded area), may be calculated. Further, instead of the condition that the difference values forming ΔRRI(t) are equal to or greater than 50 msecs, the autonomic nerve NN50 465 may be calculated based on a condition that the difference values forming ΔRRI(t) exceed 50 msecs. Further, instead of XX=50, NNXX may be calculated with XX=40, 60, 100, or the like.

The biological index calculation unit 31 stores the autonomic nerve total power 462, the autonomic nerve LF/HF 463, the autonomic nerve NN50 465, and the average RRI 464 calculated as described above in the biological index data 46 (S24 in FIGS. 4 and S56).

Therefore, the accident risk prediction model 43 can output interpretation data regarding a state of a driver from a biological index based on the intensities LF and HF such as the autonomic nerve LF/HF 463 or the like, and a biological index based on the time-domain analysis such as the autonomic nerve NN50 465. The interpretation data may include a stressed state or a relaxed state of a driver.

FIG. 5 is a flowchart showing an example of prediction processing performed by the operation support server 1. This processing is executed at a predetermined timing after the biological index data 46 is updated. The accident risk prediction unit 35 acquires the biological index data 46 up to a predetermined period from the latest data (S31).

Next, the prediction model selection unit 34 specifies the user ID 420 and the vehicle ID 423 to be analyzed from the business data 42, and selects the accident risk prediction model 43 to be used using the environmental data 47 (S32). The user ID 420 to be analyzed can be, for example, the user ID 460 of the unprocessed biological index data 46.

When a plurality of accident risk prediction models 43 exist, the prediction model selection unit 34 selects a model to be used based on the weather 473, the date and time 471, the traffic jam status 472, and the like of the environmental data 47.

Next, the accident risk prediction unit 35 inputs the biological index data 46 of the user ID to be analyzed to the selected accident risk prediction model 43, thereby calculating an accident risk (S33). The calculated accident risk is stored in the accident risk 444 of the accident risk prediction data 44.

In FIG. 15, an example of storing the accident risk 444 is shown. However, when the accident risk prediction model 43 outputs interpretation data regarding a state of a driver (a stressed state or a relaxed state) from the autonomic nerve LF/HF 463 or the like, the interpretation data can be stored in the biological index data 46.

In addition, an example of inputting the biological index data 46 to the accident risk prediction model 43 is shown above, but the present invention is not limited thereto. The environmental data 47 and the in-vehicle sensor data 40 may be inputted to the accident risk prediction model 43. For example, when the accident risk prediction model 43 outputs the interpretation data, prediction accuracy can be improved by inputting the traffic jam status or the like to the accident risk prediction model 43.

The accident risk (and the interpretation data) after the predetermined time Δt is predicted by the accident risk prediction model 43 at a predetermined timing after the biological index data 46 is updated, by the above-described processing.

FIG. 6 is a flowchart showing an example of alert generation processing performed by the operation support server 1. This processing is executed after the prediction processing shown in FIG. 5 is completed.

The accident risk notification unit 36 acquires the alert definition data 49 (S41). The accident risk notification unit 36 refers to the accident risk prediction data 44, and retrieves a driver whose value of the accident risk 444 after a predetermined time Δt is equal to or greater than a preset threshold value Th (a reference value in the drawing) (S42).

The accident risk notification unit 36 proceeds to step S44 when there is a driver whose value of the accident risk 444 after the predetermined time Δt is equal to or greater than the threshold value Th, and acquires the vehicle ID 423 of the business data 42 from an identifier of the driver whose value thereof is equal to or greater than the threshold value Th, thereby determining a vehicle having the acquired vehicle ID as an alert transmission target (S44).

The accident risk notification unit 36 acquires the environmental data 47 by the vehicle ID 470 of the vehicle 7, selects, from the alert definition data 49, the alert ID 490 satisfying the conditions of the environmental data 47 (the time condition 492, the traffic jam condition 493, and the weather condition 494) and the accident risk condition 491, and outputs an accident risk alert (not shown) designated by the alert ID 490 and the comment 496 of the selected record (S45).

The accident risk notification unit 36 acquires the position 402 of the vehicle 7 from the in-vehicle sensor data 40, adds the position information of the vehicle 7, and generates an alert.

An alert is transmitted to the vehicle 7 of a driver who is predicted to have an accident risk equal to or greater than the threshold value Th after the predetermined time Δt, by the above-described processing. In the vehicle 7 receiving the alert, the prediction result notification device 9 notifies the driver of the alert. Further, in the operation support server 1, the accident risk notification unit 36 displays the vehicle 7 to which the alert is transmitted on the display of the input and output device 5.

In the alert definition data 49 in FIG. 14, an example of determining the comment 496 and the alert ID 490 by the accident risk condition 491, the environmental condition, and the priority 495 is shown, but the present invention is not limited thereto. For example, when the accident risk prediction model 43 outputs interpretation data regarding a state of a driver, a condition for determination of the alert ID may be set based on the interpretation data.

As an example, in the case in which the accident risk 444 is the same, when the interpretation data shows a stressed state or a relaxed state, the alert ID 490 when the accident risk increases in the stressed state and the alert ID 490 when the accident risk increases in the relaxed state are set as different alerts. Thus, highly accurate prediction can be achieved by adding the interpretation data to the value of the accident risk 444.

FIG. 16A is a diagram showing an example of a prediction result display screen 600 outputted by the accident risk notification unit 36 to the display of the input and output device 5. An icon 602 of the vehicle 7 to be managed is displayed on the map on the prediction result display screen 600 outputted by the accident risk notification unit 36, and an alert icon 601 is added to the icon 602 to which the alert is issued.

In the vicinity of the alert icon 601, a driving state 603 of a driver having increased accident risk is displayed, and the amount of work and the number of breaks of the driver can be notified to a manager or the like.

Further, the manager can check the accident risks of a plurality of drivers by listing the same on the map, and can select a driver having a high accident risk and remotely give an instruction to the driver.

In the illustrated example, an example of displaying the position of the vehicle 7 and the status of the driver on the map is shown, but the present invention is not limited thereto. Notification may be performed with character information such as a list or the like.

Additionally, when interpretation data of a driver whose accident risk is predicted to increase can be obtained from the autonomic nerves LF/HF 463 or the like, the accident risk notification unit 36 displays the interpretation data in the driving state 603, thereby allowing a manager or the like to grasp a stressed state and a relaxed state of the driver.

FIG. 16B is a diagram showing an example of a prediction result display screen 650 outputted by the prediction result notification device 9. The prediction result notification device 9 has a display (not shown) and displays the prediction result display screen 650 when an alert is received from the operation support server 1.

The prediction result display screen 650 includes an area 651 in which an accident risk alert is displayed and an area 652 in which a comment is displayed. The driver can recognize the accident risk by visually recognizing the prediction result display screen 650 of the prediction result notification device 9.

As described above, the operation support system of the embodiment inputs the biological index data 46 calculated by the operation support server 1 from the heart rate data of the biological sensor 12 to the accident risk prediction model 43, and predicts the accident risk 444 after the predetermined time Δt. Accordingly, a state in which a traffic accident is likely to occur is predicted in advance depending on an autonomic nervous state of a driver of the vehicle 7, thereby making it possible to give the driver feedback such as recommending a break or the like.

In the first embodiment, an example of applying the present invention to the operation support system configured to manage the vehicle 7 is shown, but the present invention is not limited thereto. For example, instead of the vehicle 7, the present invention can be applied to a moving body requiring a driver or a pilot such as a railway vehicle, a ship, or an aircraft.

In the first embodiment, an example of generating the accident risk definition model 48 from the in-vehicle sensor data 40-$m1$ collected in the past and the hazard occurrence data 45 is shown, but the present invention is not limited thereto. For example, from the new in-vehicle sensor data 40 in which business is completed, a portion determined to be hazardous by a driver may be specified to generate the new hazard occurrence data 45, and the new hazard occurrence data 45 may be added as learning data. Thereafter, the accident risk definition model 48 may be relearned. In this case, the accident risk prediction model 43 is also generated again.

Second Embodiment

FIG. 17 shows a second embodiment, and is a block diagram showing an example of a configuration of an operation support system. In the embodiment, the biological index calculation unit 31, the accident risk prediction unit 35, and the biological index data 46 are disposed in the driving data collection device 10 of the vehicle 7, and an accident risk is predicted by an accident risk prediction model 43A selected by the prediction model selection unit 34 of the operation support server 1.

The driving data collection device 10 of the vehicle 7 calculates the biological index data and predicts an accident risk, and the accident risk is transmitted to the operation support server 1. In the operation support server 1, when the accident risk after the predetermined time Δt becomes equal to or greater than the threshold value Th, the accident risk notification unit 36 outputs an alert to the corresponding vehicle 7 in the same manner as in the first embodiment.

In the embodiment, it is possible to reduce the load on the operation support server 1 and increase the number of vehicles 7 managed by the operation support server 1 by allowing the vehicle 7 side to calculate a biological index and predict an accident risk.

Third Embodiment

Next, a third embodiment of the present invention will be described. In PTL 2, provided is a means of recognizing a deviation from a normal internal state of a driver by comparing a traveling environment recognized by sensing the external environment of a moving body and a risk recognition state of a driver estimated as an internal state from a driving operation of a driver.

However, it is not possible to detect a state which does not appear in the driving operation but requires attention (a hazardous state in a broad sense) by performing a state estimation about a relationship between the driver's driving operation and the external environment and recognizing a deviation from the normal internal state of the driver (a hazardous state in a narrow sense). Therefore, there is a problem that it is difficult to take measures to avoid a hazardous state in a broad sense in advance.

This embodiment has been made in view of the above-described problems, and, in order to detect a hazardous state in a broad sense and avoid the same in advance, it is an object of the present invention to detect a hazardous state in a broad sense based on an individual difference for each driver using biological data, and to determine whether or not an alert is issued based on the detection result.

<System Configuration>

FIG. 18 shows the third embodiment of the present invention, and is a block diagram showing an example of a main configuration of an operation support system. The operation support system of the embodiment includes the operation support server 1 configured to support operation of one or more vehicles 7 via a network 14.

The vehicle 7 includes the in-vehicle sensor 8 configured to detect a traveling state, the biological sensor 12 configured to detect biological sensor data 163 of a driver, the driver ID reader 11 configured to specify a driver, the driving data collection device 10 configured to collect the detected traveling state and biological sensor data 163 and the driver ID and to transmit the same to the operation support server 1, the prediction result notification device 9 configured to receive a warning in accordance with a traffic accident risk of a driver (hereinafter referred to as an accident risk) from the operation support server 1 and to give the warning to the driver, and a business state input device 130 configured to receive the input of measurement status of a biological index data 164.

In the illustrated example, although the driving data collection device 10, the prediction result notification device 9, the business state input device 130, and the driver ID reader 11 are independent devices, the same can be configured as one portable terminal. In this case, the portable terminal functions as a driving data collection unit, a prediction result notification unit, a business state input unit, and a driver ID reading unit.

The in-vehicle sensor 8 can include the global navigation satellite system (GNSS) 81 configured to detect position information of a vehicle, the acceleration sensor 82 configured to detect the behavior and speed of a vehicle, and the camera 83 configured to detect a traveling environment as an image.

The in-vehicle sensor 8 is not limited thereto, but can use a ranging sensor configured to detect an object around a vehicle and/or a distance thereof, a steering angle sensor configured to detect a driving operation, and an angular velocity sensor configured to detect a turning operation of a vehicle. The acceleration sensor 82 is preferably a triaxial acceleration sensor.

The biological sensor 12 includes the heart rate sensor 121 configured to detect heart rate data and the acceleration sensor 122 configured to detect movement of a driver. The heart rate sensor 121 can use a sensor configured to detect a heart rate based on an electrocardiogram, a pulse wave, a cardiac sound, and the like.

The biological sensor 12 is not limited thereto, but can adopt a sensor configured to detect the amount of sweating, body temperature, blinking, eye movement, myoelectricity, brain waves, and the like. As the biological sensor 12, in addition to a wearable device that can be worn by a driver, it is possible to use a sensing device attached to the inside of a vehicle such as a steering wheel, a seat, a seat belt, and the like, and an image recognition system configured to capture the facial expression and behavior of a driver and to analyze a captured image thereof.

The driver ID reader 11 reads a card in which a driver identifier is recorded. The driving data collection device 10 collects data from the in-vehicle sensor 8 and the biological sensor 12 at a predetermined cycle, and transmits the collected data to the operation support server 1 via the network 14.

In the illustrated example, the driver ID reader 11 is configured as a device configured to read the card in which the driver identifier is recorded, but may have a different configuration. For example, when the driver ID reader 11 is configured as one portable terminal and the portable terminal functions as a driver ID reading unit, the driver ID may be read by allowing a driver himself or herself to input a driver identifier, or the driver ID may be read by identifying the driver by a well-known face recognition technique using a camera provided in the portable terminal.

The business state input device 130 receives a business state of a driver such as driving, resting, and napping, and transmits the business state to the operation support server 1.

The operation support server 1 is a computer including the processor 2, the memory 3, the storage device 4, the input and output device 5, and the communication device 6. The memory 3 loads, as a program, each functional unit of a biological index calculation unit 131, an accident risk definition generation unit 132, an accident risk estimation unit 133, a biological state estimation model generation unit 134, an accident risk prediction model generation unit 135, a model selection unit 136, a hazard prediction unit 137, a warning presentation unit 138, and a data collection unit 139. Each program is executed by the processor 2. Details of each functional unit will be described later.

The processor 2 operates as a functional unit configured to provide a predetermined function by executing processing according to the program of each functional unit. For example, the processor 2 functions as the biological index calculation unit 131 by executing a biological index calculation program. The same is true for other programs. Furthermore, the processor 2 also operates as a functional unit configured to provide respective functions of a plurality of pieces of processing executed by respective programs. A computer and a computer system are a device and a system including these functional units.

The storage device 4 stores data used by each functional unit. The storage device 4 stores in-vehicle sensor data 161, biological sensor data (first biological data) 163, business and environment data 174, an accident risk prediction model 171, accident risk prediction data 166, hazard occurrence data 162, biological index data 164, an accident risk definition model 170, alert definition data 172, accident risk estimation data 165, countermeasure plan data 173, a biological state estimation model 169, person's severity level data 167, a combination table 168, attribute information data 175, and learning information data 176.

As described later, the in-vehicle sensor data 161 includes in-vehicle sensor data 161-1 (first in-vehicle sensor data) to be used when the accident risk definition model 170 is generated and in-vehicle sensor data 161-2 (second in-vehicle sensor data) to be used when the accident risk prediction model 171 is generated. In the following description, when the in-vehicle sensor data is not distinguished, a reference numeral "161" in which "-" and a subsequent reference numeral are omitted is used.

As described later, the biological index data 164 includes biological index data 164-1 (first biological index data) to be used when the accident risk prediction model 171 is generated, biological index data 164-2 (second biological index data) to be used when the accident risk prediction data 166 is generated by inputting the biological index data 164-2 to the accident risk prediction model 171, and biological index data 164-3 (third biological index data) to be used when the biological state estimation model 169 is generated. In the following description, when the biological index data is not distinguished, a reference numeral "164" in which "-" and a subsequent reference numeral are omitted is used. Details of each piece of data will be described later.

The input and output device 5 includes an input device such as a mouse, a keyboard, a touch panel or a microphone and an output device such as a display and a speaker. The communication device 6 communicates with a vehicle via the network 14.

<Processing Outline>

FIG. 19 is a diagram showing an outline of processing performed by the operation support system. The illustrated example shows an example formed of a learning phase performed before the start of operation of the vehicle 7 and an operation phase performed during operation of the vehicle 7.

First, the operation support system generates, in the operation support server 1, the accident risk prediction model 171 and the biological state estimation model 169 which are required to predict a hazardous state of a driver who is driving the vehicle 7.

First, the accident risk definition generation unit 132 inputs the preset hazard occurrence data 162 and the in-vehicle sensor data 161-1 collected in the past, thereby generating the accident risk definition model 170 configured to estimate the probability of the hazard occurrence as an accident risk (S101). The time series of the in-vehicle sensor data 161-1 and the time series of the hazard occurrence data 162 are the same time series.

The accident risk definition model 170 estimates an accident risk which is the probability of occurrence of a hazardous event by inputting the in-vehicle sensor data 161-2 (described later) indicating the traveling state of the vehicle in the past. In addition, a value of the accident risk is shown as a percentage below.

The hazard occurrence data 162 is data obtained by extracting an event determined to be hazardous based on the in-vehicle sensor data collected in the past, and specifically, is data preset from the type of an event and the date and time of occurrence thereof by allowing a driver or a manager to determine an incident such as a sudden braking or a sharp turning and an event leading to an incident, or by allowing a commercially available in-vehicle warning device or AI to determine the incident and the event. Furthermore, an importance level of the hazard occurrence data 162 may be set for each incident.

In the embodiment, an incident is defined as an event leading to a traffic accident. Additionally, an event leading to an incident indicates a state in which a driver is nervous or startled. Furthermore, an example in which hazard increases as an importance level increases is shown. In the following description, an incident or an event leading to an incident is defined as a hazardous event.

The hazardous state in the narrow sense described in the above subject can include the above-described incident, and the hazardous state in the broad sense described above can include an event leading to the above-described incident.

The accident risk definition model 170 is a machine learning model, and estimates an accident risk in which a hazardous event occurs by inputting the in-vehicle sensor data 161-2. A well-known or known method such as a support vector machine, a neural network, and logistic regression can be used for the machine learning model. Further, a plurality of accident risk definition models 170 may be generated for each type of the hazardous event.

Next, the accident risk estimation unit 133 inputs the in-vehicle sensor data 161-2 collected in the past to the accident risk definition model 170, thereby generating the accident risk estimation data 165 configured to estimate accident risks in which a hazardous event occurs in time series (S102).

The accident risk estimation data 165 is data in which the probability that a hazardous event occurs with respect to the in-vehicle sensor data 161-2 is generated in the same time series as the in-vehicle sensor data 161-2.

After that, the accident risk prediction model generation unit 135 inputs the accident risk estimation data 165 and the past biological index data 164-1, predicts and outputs an accident risk after a predetermined time from the biological index data 164-2 (described later) of a driver of the traveling vehicle 7, and generates the accident risk prediction model 171 (S104). The past biological index data 164-1 is calculated by the biological index calculation unit 131 from the past biological sensor data 163 corresponding to the in-vehicle sensor data 161-2 collected in the past.

In the embodiment, the biological index data 164-1 calculated from the biological sensor data 163 collected in the past can be calculated by using, for example, an average heart rate calculated from heart rate data of a driver, the maximum Lyapunov exponent calculated by nonlinear analysis of heart rate data series, frequency-domain analysis of heart rate interval data extracted from heart rate data, or an autonomic nervous function index (LF/HF or the like). The autonomic nervous function index (LF/HF or the like) can be calculated by a method such as time-domain analysis and nonlinear analysis.

The biological index data 164-1 is a biological index calculated by the biological index calculation unit 131 from the past biological sensor data 163 corresponding to the time series of the in-vehicle sensor data 161-2.

The accident risk prediction model 171 is formed of a well-known or known machine learning model, and outputs an accident risk after a predetermined time by inputting the biological index data 164-2 of a driver who is driving a vehicle. The biological index data 164-2 of the driver who is driving the vehicle is a biological index calculated by the biological index calculation unit 131 from the biological sensor data 163 of the driver, and is received from the traveling vehicle 7 by the operation support server 1.

As the accident risk prediction model 171, a plurality of models may be generated in advance according to a type of accident risk, a type of biological index data to be used, and a traveling environment and a predetermined time of a vehicle to which prediction is applied. By generating a plurality of models, it is possible to select an appropriate model in the hazard prediction processing and use the same properly.

In addition, a plurality of models may be generated according to the attribute information data 175 configured to store business characteristics of a driver (general road traveling, high-speed traveling, continuous work day and night, and the like), driving experience of a driver (years of driving, driving skills, type of license), and health characteristics of a driver (gender, amount of sleep, and the like).

Next, the biological state estimation model generation unit 134 inputs the biological index data 164-3 measured in the past, and generates the biological state estimation model 169 configured to estimate and output a person's severity level. Here, the person's severity level indicates how much the input (the current biological index data 164-2) deviates from the biological index data 164-3 measured in the past (S103). A degree of the deviation of the current biological index data 164-2 from the biological index data 164-3 measured in the past may be represented as a degree of abnormality.

The biological state estimation model 169 is formed of a well-known or known statistical model or a machine learning model. A plurality of biological state estimation models 169 are typically generated for each type of the biological index data 164-3. Here, the biological state estimation model 169 is an unsupervised model configured to input a certain type of biological index data 164-3 and to output a statistic showing a degree of abnormality (the person's severity level) based on the biological index data 164-3 used for model generation.

As a statistical model, for example, it is possible to use a statistical model configured to output a z-score whose input is normalized using an average value and a standard deviation of the biological index data 164-3 used for model generation, a statistical model configured to normalize an output in the range of 0 to 1 using the maximum and minimum values of the biological index data 164-3 used for model generation, a statistical model configured to output a rate of change from a statistic value of the biological index data 164-3 used for model generation based on the statistic thereof, and a statistical model configured to output a quantile on a data distribution estimated from the biological index data 164-3 used to generate the biological state estimation model 169.

Further, as a machine learning model, for example, it is possible to use an abnormality detection model in which a data distribution is estimated nonparametrically from the biological index data 164-3 used to generate the biological state estimation model 169, and a distance of the distribution from a cluster center is outputted.

In addition to the unsupervised biological state estimation model 169, the supervised biological state estimation model 169 can be adopted. In this case, it is possible to configure the biological state estimation model 169 using a well-known or known statistical model or machine learning model configured to estimate the learning information data 176 as an objective variable. Here, the learning information data 176 collects the number of blinks (number of nictation), which is an index of driver drowsiness and driver's arousal state estimated by a well-known or known method, and a subjective fatigue level in which a driver answers his or her subjective fatigue level with a visual analogue scale (VAS). In this case, for example, a regression model or the like can be adopted as a statistical model, and a support vector machine, a neural network, and the like can be adopted as a machine learning model.

The biological index data 164-3 used as an input of the biological state estimation model 169 is typically univariate, but may be multivariate. When the input is multivariate, it is desirable to input a combination of biological index data types that are easy to be used to generate a countermeasure plan to avoid a hazardous state in warning presentation processing to be described later. In this case, the biological state estimation model 169 can be formed of well-known methods such as a multiple regression model, the Mahalanobis-Taguchi system, and multivariate statistical process management.

The biological state estimation model 169 may be generated for each driver, or a plurality of driver groups may be combined to generate one biological state estimation model 169. When a plurality of driver groups are combined, it is desirable to generate the biological state estimation model 169 for a group of drivers showing similar biological responses because there are large individual differences in living organisms.

By generating the biological state estimation model 169 from a plurality of driver groups showing similar biological responses, it is possible to absorb individual differences in the biological response and to shorten the time of measuring the data required to generate the biological state estimation model 169.

Further, after the required amount of data is measured, it is desirable to switch from the biological state estimation model 169 generated from a plurality of driver groups showing showing the similar biological responses to the biological state estimation model 169 generated only from a target driver. Thus, it is possible to output the person's severity level in consideration of a biological response of an individual.

Next, the operation support system uses the generated accident risk prediction model 171 and the biological state estimation model 169 using the operation support server 1 to predict the probability of occurrence of a hazardous event of a driver who is actually driving the vehicle 7.

First, the hazard prediction unit 137 inputs, to the biological index calculation unit 131, the biological sensor data 163 such as heart rate data measured by the biological sensor 12 received from the vehicle 7 by the data collection unit 139, and calculates the biological index data 164-2 (S105).

When a plurality of accident risk prediction models 171 and biological state estimation models 169 exist, the hazard prediction unit 137 selects the accident risk prediction model 171 and the biological state estimation model 169 in accordance with the business and environment data 174 and the attribute information data 175 with the model selection unit 136.

Thereafter, the hazard prediction unit 137 inputs the biological index data 164-2 to the accident risk prediction model 171 to predict (generate) the accident risk prediction data 166 (S106A). The hazard prediction unit 137 inputs the biological index data 164-2 to the biological state estimation model 169 to calculate the person's severity level data 167 for each biological index data type (S106B).

The hazard prediction unit 137 extracts the type (a contribution index) of the biological index data 164-2 contributing to the prediction of the accident risk prediction data 166, collates the accident risk prediction data 166, the accident risk prediction model 171 used to calculate the accident risk prediction data 166, the contribution index, and the person's severity level data 167 of the contribution index, and stores the same in the combination table 168 (S107A).

In extracting the contribution index, the hazard prediction unit 137 extracts the contribution index from the biological index data 164-2, the accident risk prediction data 166, and the accident risk prediction model 171 used to calculate the accident risk prediction data 166.

For example, when a linear model such as logistic regression is used as the accident risk prediction model 171, the hazard prediction unit 137 can simply extract, as the contribution index, a biological index data type that maximizes the product of a regression coefficient and the biological index data 164-2.

Further, when a neural network or the like is used as the accident risk prediction model 171, for example, the hazard prediction unit 137 can calculate the contribution of each biological index data 164-2 using SHapley Additive exPlanations (SHAP), which is a known method used to ensure the description of a machine learning model, and can extract the biological index data 164-2 having the maximum contribution as a contribution index.

The warning presentation unit 138 determines issuance (hereinafter referred to as issuance determination) based on the accident risk and the person's severity level stored in the combination table 168 (S107B). When determining that a driver is in a hazardous state in a broad sense, the warning presentation unit 138 generates a countermeasure plan to avoid the hazardous state in the broad sense (S107C).

In the issuance determination, when the accident risk or the person's severity level exceeds a predetermined threshold value, respectively, or when values related to the accident risk and the person's severity level exceed a predetermined threshold value, the warning presentation unit 138 determines that the driver is in a hazardous state (a hazardous event) in a broad sense. In the former case, the warning presentation unit 138 may not set a threshold value of either the accident risk or the person's severity level during the issuance determination.

For example, when the warning presentation unit 138 sets a threshold value only for the accident risk, it is possible to issue a notification for a scene generally determined to have a high accident risk. Further, when the warning presentation unit 138 sets a threshold value only for the person's severity level, it is possible to issue a notification for an abnormality in the biological index data 164-2 such as a sudden change in a physical condition of an individual driver. A threshold value may be set not only for the corresponding accident risk and the record of the person's severity level, but also for the time series of the accident risk and the person's severity level.

In the generation of the countermeasure plan executed by the warning presentation unit 138, the countermeasure plan to avoid a hazardous state in a broad sense is generated based on the combination table 168 and the countermeasure plan data 173. From past knowledge, a method of physiologically interpreting changes in certain types of biological index data 164-2 and a method of changing certain types of biological index data 164-2 are known.

The countermeasure plan data 173 stores a physiological interpretation when a value increases or decreases for each type of the biological index data 164-2 and a method for increasing or decreasing the value. Since the combination table 168 stores a contribution index contributing to the prediction of an accident risk, a physiological interpretation corresponding to the contribution index (described later) and a method of increasing or decreasing the contribution index are acquired, thereby making it possible to generate a countermeasure plan to avoid a hazardous state in a broad sense depending on a state of a driver.

For example, when the contribution index is LF/HF, which is an autonomic nervous function index, the LF/HF is the positive direction, and the person's severity level is high, this state can be physiologically interpreted as an overstressed state. Here, the warning presentation unit 138 may generate a countermeasure plan to encourage relaxation, such as "let's breathe slowly" in order to reduce the LF/HF of the driver.

Further, when the contribution index is an average heart rate, the average heart rate tends to decrease, and the person's severity level is high, this state is physiologically interpreted as increasing drowsiness, and the warning presentation unit 138 may generate a countermeasure plan to encourage elimination of drowsiness, such as "let's stop once at the next convenience store, go out of the vehicle, and stretch your body".

In generating the countermeasure plan, the warning presentation unit 138 can add information based on the person's severity level of the contribution index to the countermeasure plan. Although it is difficult to convey the hazard to a driver himself or herself receiving a warning only by a warning based on an accident risk, the warning is given in a form understandable to the driver himself or herself based on the person's severity level, and as such, it is expected that an acceptance degree of a driver with respect to a warning will be improved. Furthermore, in generating the counter- measure plan, the warning presentation unit 138 can add information based on the business and environment data 174 and the attribute information data 175 to the countermeasure plan.

After the countermeasure plan is generated, the warning presentation unit 138 transmits a warning as an alert or a message including the countermeasure plan to the vehicle 7 determined to be in a hazardous state in a broad sense (S108). Further, the warning presentation unit 138 may transmit the warning not only to the vehicle 7 but also to a driver manager, and may display the warning on the display of the input and output device 5. In this case, the contents displayed on the display can include an image including the position information of the driver or the like.

When the vehicle 7 receives the warning from the operation support server 1, the prediction result notification device 9 outputs the alert and transmits the alert or the message to the driver.

The operation support server 1 determines a hazardous state in a broad sense based on an accident risk after a predetermined time predicted using the accident risk prediction model 171 and a person's severity level of the biological index data 164-2 estimated using the biological state estimation model 169, thereby making it possible to detect a hazardous state in a broad sense by absorbing individual differences for each driver included in the biological index data 164-2.

Additionally, when determining a hazardous state in a broad sense, the operation support server 1 generates a countermeasure plan to avoid the hazardous state in the broad sense based on a contribution index and a person's severity level of the contribution index, and transmits a warning including the countermeasure plan to a prediction result notification device 9 of the corresponding vehicle 7 and a display of the input and output device 5 thereof. Thus, the operation support server 1 can give a warning to a driver and a driver manager before an accident risk increases, and take measures to avoid a hazardous state in a broad sense.

As described above, the operation support server 1 avoids a hazardous state in a broad sense in advance and prevents a driver from falling into a hazardous state in a narrow sense, thereby making it possible to support the safe operation of each vehicle 7.

<Details of Processing>

FIG. 20 is a flowchart showing an example of generation processing of the accident risk prediction model 171. This processing is performed before the biological index data 164-2 is received from the vehicle 7 configured to detect the hazard during traveling (a learning stage in FIG. 19), and the accident risk prediction model 171 is generated in advance.

The accident risk definition generation unit 132 generates the accident risk definition model 170 by inputting the hazard occurrence data 162 collected in the past and the corresponding in-vehicle sensor data 161-1 (S101).

Next, the accident risk prediction model generation unit 135 inputs the in-vehicle sensor data 161-2 collected in the past to the generated accident risk definition model 170, thereby generating the accident risk estimation data 165 (S102).

Next, the accident risk prediction model generation unit 135 generates the accident risk prediction model 171 from the biological index data 164-1 corresponding to the in-vehicle sensor data 161-2 collected in the past and the accident risk estimation data 165 (S104). In this case, the accident risk prediction model generation unit 135 may generate the accident risk prediction model 171 for each similar business characteristic or environmental characteristic based on the business and environment data 174, and may add the information to the accident risk prediction model 171 as meta information.

By the above-described processing, the operation support server 1 generates the accident risk definition model 170 to generate the accident risk estimation data 165, and then generates the accident risk prediction model 171 from the biological index data 164-1 corresponding to the accident risk estimation data 165 in time series.

Further, the above-described processing is performed every time the amount and type of the hazard occurrence data 162 increase by a certain amount, every time the accident risk estimation data 165 with a high accident risk increases by a certain degree, or at a fixed frequency, and the accident risk definition model 170 and the accident risk prediction model 171 are updated each time.

FIG. 21 is a flowchart showing an example of generation processing of the biological state estimation model 169. This processing is performed before the hazard during traveling is predicted for a certain vehicle 7 (a learning stage in FIG. 19), and the biological state estimation model 169 is generated for each type of the biological index data 164-3.

The biological state estimation model generation unit 134 first extracts a driver group showing a similar biological response as a driver group used to generate the biological state estimation model 169 (S111). Typically, clustering is performed using a well-known or known method using the average of certain types of biological index data 164-3, daily statistics thereof such as a standard deviation, a median, and a quantile, and weekly and monthly statistics thereof, thereby extracting a driver group showing a similar biological response.

In this case, the biological state estimation model generation unit 134 may add, as an input for clustering, information included in the business and environment data 174, gender included in the attribute information data 175, and information on the age stratified based on age, in addition to the biological index data 164-3.

In addition, when selecting the biological index data 164-3 to be inputted to perform clustering, the biological state estimation model generation unit 134 may select only the biological index data 164-3 measured under the same measurement conditions based on the learning information data 176, and may input only the biological index data 164-3 in a period stored in the learning information data 176. Accordingly, it is expected that measurement conditions are controlled and thus variations in the biological index data 164-3 are prevented.

The biological state estimation model generation unit 134 may further extract only a specific driver instead of a plurality of driver groups when a sufficient amount of biological index data 164-3 can be measured with respect to the specific driver. Accordingly, it is possible to estimate a person's severity level matched with characteristics of a specific individual.

Next, the biological state estimation model generation unit 134 inputs the biological index data 164-3 collected in the past to the extracted driver group, and generates the biological state estimation model 169 for each type of the biological index data 164-3 (S103).

In this case, the biological state estimation model generation unit 134 may select only the biological index data 1643 measured under the same measurement conditions based on the learning information data 176 as in the driver extraction, and may input only the biological index data 164-3 in the period stored in the learning information data 176.

When generating a supervised model as the biological state estimation model 169, the biological state estimation model generation unit 134 inputs an objective variable in a period stored in the learning information data 176 and the corresponding biological index data 164-3, thereby generating the biological state estimation model 169 for each type of the biological index data 164-3.

In this case, the biological state estimation model generation unit 134 may add, as meta information, information on the type of biological index data 164-3 to be inputted and information on similar biological characteristics to the biological state estimation model 169.

After extracting the driver group showing the similar biological response characteristics by the above-described processing, the biological state estimation model 169 is generated for each type of the biological index data 164-3 from the biological index data 164-3 of the extracted driver group.

Further, the processing generated from the plurality of drivers is performed every time the number of target drivers increases by a fixed amount, every time the biological index data 164-3 increases by a fixed amount, or every fixed period, and as such, the biological state estimation model 169 is updated. Further, the processing generated from a specific driver is performed every time the biological index data 164-3 increases by a fixed amount or every fixed period, and as such, the biological state estimation model 169 is updated.

The biological index data 164-3 used to generate the biological state estimation model 169 is different from the biological index data 164-1 used to generate the accident risk prediction model 171 in that it is not necessary to deal with the in-vehicle sensor data 161-2, it is not necessary to deal with the case in which there is a high risk of accidents, and there are few restrictions on the measurement scene.

Therefore, since it is easy to measure the biological index data 164-3 used to generate the biological state estimation model 169, data can be measured in a short period of time compared with the generation of the accident risk prediction model 171, and therefore, it can be expected that the update frequency can be set high.

Furthermore, since a hazardous state in a broad sense rarely occurs, it takes time to construct the accident risk prediction model 171 from only a plurality of driver groups having similar biological responses. On the other hand, in the embodiment, since individual differences in biological responses among a plurality of drivers are absorbed not in the accident risk prediction model 171 but in the biological state estimation model 169, it is possible to generate a model using the data of drivers whose biological responses are not similar in generating the accident risk prediction model 171. In generating the biological state estimation model 169, the model can be generated only from the data of drivers having similar biological characteristics that can be easily collected during driving.

As described above, the methods of absorbing individual differences in biological responses in the generation of the accident risk prediction model 171 can be compared with each other, and it is possible to shorten the time required for model generation required to implement the hazard prediction processing in the embodiment.

FIG. 22 is a flowchart showing an example of calculation processing of the biological index data 164. This processing is performed by the biological index calculation unit 131 every time data is received from the vehicle 7.

The data collection unit 139 of the operation support server 1 receives the data of the in-vehicle sensor 8 and the biological sensor 12 from the operation data collection device 10 of the vehicle 7 (S121).

The data collection unit 139 stores the heart rate data detected by the heart rate sensor 121 and the acceleration data detected by the acceleration sensor 122 in the biological sensor data 163 (S122). The data of the in-vehicle sensor 8 is stored in the in-vehicle sensor data 161.

Next, the biological index calculation unit 131 calculates the biological index data 164 by inputting the biological sensor data 163 using a method described later in FIG. 23 (S123). The biological index calculation unit 131 stores the calculated data in the biological index data 164 (S124). The biological index data 164 is calculated from the biological sensor data 163 by the above-described processing.

FIG. 23 is a flowchart showing an example of calculation processing of the biological index data 164 using the heart rate data. This processing is performed by the biological index calculation unit 131 every time the biological sensor data 163 is stored.

Since the calculation processing of the biological index data 164 using the heart rate data is performed by a well-known or known method, only the outline thereof will be described below. First, the biological index calculation unit 131 reads the heart rate data in the biological sensor data 163 (S131). The heart rate data refers to data capable of extracting a heart rate interval acquired by the heart rate sensor 121 from a driver who is driving a vehicle. Specifically, examples of the heart rate data include electrocardiographic data, pulse wave data, cardiac sound data, and the like.

Subsequently, the biological index calculation unit 131 extracts an inter beat interval (IBI) from the heart rate data and calculates the time series thereof (S132). In the case of electrocardiographic data, the IBI may particularly calculate an R-R interval (RRI) time series which is using an interval of an electrocardiographic R-wave. In the following description, the RRI is particularly mentioned as an example.

The biological index calculation unit 131 calculates an autonomic nervous function index by performing analysis as necessary from the RRI. Examples of the analysis as necessary include frequency-domain analysis, time-domain analysis, and RRI nonlinear-domain analysis.

The biological index calculation unit 131 calculates a frequency-domain index from an RRI time series via power spectral density in the frequency-domain analysis (S133). Since the RRI time series is unequal interval time-series data, the power spectral density (PSD) is calculated using an autoregressive model or a maximum entropy method after performing resampling at regular intervals by spline interpolation or the like, or using a known method such as the Lomb-Scargle method capable of using unequal interval data.

The biological index calculation unit 131 calculates, among the calculated PSDs, for example, an integral value LF in a low-frequency region of 0.05 Hz to 0.15 Hz, an integral value HF in a high-frequency region of 0.15 Hz to 0.40 Hz, TP which is the sum of LF and HF, LF/HF obtained by dividing LF by HF, and LFnu obtained by dividing LF by TP as a percentage as a frequency-domain index of an autonomic nervous function index.

In the time-domain analysis, the biological index calculation unit 131 calculates a time-domain index by calculating statistics of an RRI time series and a ΔRRI time series which is a difference series of the adjacent RRIs (S134). For example, an average heart rate, which is the reciprocal of an average value of the RRI time series, and SDNN, which is the standard deviation of the RRI, are calculated. Additionally, from the ΔRRI time series, for example, NN50, which is the total number of data in which an absolute value of a difference value forming the ΔRRI time series exceeds 50 msec, pNN50 obtained by dividing NN50 by the total number of data in the ΔRRI time series, and SDSD, which is the standard deviation of ΔRRI, are calculated as a time-domain index of an autonomic nervous function index.

The biological index calculation unit 131 calculates nonlinear feature quantities by various methods in the RRI nonlinear-domain analysis (S135). The biological index calculation unit 131 calculates, for example, an elliptical area S obtained by elliptically approximating a plotted region through the Poincare plot analysis configured to plot an RRI time-series RRI(t) on the X-axis and a time-series RRI(t+1) that advances the RRI time series by one hour on the Y-axis. In addition, the biological index calculation unit 131 calculates α1 and α2 by similar entropy and Detrended Fluctuation Analysis, and tone and entropy based on tone-entropy analysis as an RRI nonlinear-domain index of the autonomic nervous function index.

Further, the biological index calculation unit 131 can calculate a heart rate nonlinear-domain index by performing heart rate nonlinear-domain analysis on the heart rate data before RRI extraction is performed (S136). For example, the biological index calculation unit 131 calculates a correlation dimension and a maximum Lyapunov exponent of the heart rate data by applying chaos analysis to the heart rate data as the heart rate nonlinear-domain index of the autonomic nervous function index.

Since the calculated autonomic nervous function index reflects a biological state of a driver controlled by an autonomic nervous system, by calculating an index of measuring the biological state of the driver, which is necessary to be provided to the driver as a countermeasure plan to avoid a hazardous state in a broad sense, it is possible to present a warning according to the biological state. For example, since LF/HF is an index configured to measure the balance between sympathetic activity that mainly increases in a stressed state or a tensioned state and parasympathetic activity that mainly increases in a relaxed state, the biological index calculation unit 131 calculates LF/HF, thereby making it possible to give a warning based on a tension-relaxation state of a driver.

Thereafter, the biological index calculation unit 131 collectively stores a group of the calculated autonomic nervous function indexes in the biological index data 164 (S124). The autonomic nervous function index is calculated from the heart rate data in the biological sensor data 163 and stored as the biological index data 164, by the above-described processing.

The biological index calculation unit 131 may execute the processing of steps S133 to S136 in parallel or sequentially.

FIG. 24 is a flowchart showing an example of hazard prediction processing performed by the operation support server 1. This processing is executed at a predetermined timing such as every time the biological index data 164-2 is updated. The hazard prediction unit 137 acquires the biological index data 164-2 from the latest period to a predetermined period (S112).

Next, the model selection unit 136 specifies a driver ID to be analyzed and a vehicle ID from the business and environment data 174, and selects the accident risk prediction model 171 and the biological state estimation model 169 based on the business and environment data 174 (S113 and S114). In selecting the accident risk prediction model 171, for example, the model to be used is selected based on a vehicle body size, weather, a traffic jam status, and the like of the business and environment data 174.

In selecting the biological state estimation model 169, for example, the model to be used by the model selection unit 136 is selected based on information on the biological state estimation model 169 corresponding to the driver ID stored in the attribute information data 175.

Next, the hazard prediction unit 137 inputs the biological index data 164-2 of the driver ID to be analyzed to the selected accident risk prediction model 171 to predict an accident risk, and stores the predicted accident risk in the accident risk prediction data 166 (S106A). As described above, an example of inputting the biological index data 164-2 to the accident risk prediction model 171 is shown, but the present invention is not limited thereto. Here, the business and environment data 174 and the attribute information data 175 may be added to the input of the accident risk prediction model 171.

For example, by inputting driving skill information obtained by driving aptitude diagnosis or the like included in the attribute information data 175, and personality temperament information obtained by Temperament and Character Inventory (TCI), Temperament Evaluation of the Memphis, Pisa, Paris, and San Diego Autoquestionnaire (TEMPS-A), Ten Item Personality Inventory for measuring Big Five Personality, and NEO-FFI, the driving skills and personality of a driver are taken into consideration, thereby making it possible to implement more highly accurate accident risk prediction.

In addition, the hazard prediction unit 137 inputs biological index data 164-2 of the driver ID to be analyzed to the selected biological state estimation model 169 to estimate a plurality of person's severity levels for each biological index data type, and stores the estimated person's severity levels in the person's severity level data 167 (S106B). In the above description, an example of inputting the biological index data 164 and the biological index data 164-2 as univariate is shown, and in addition thereto, for example, the hazard prediction unit 137 may input the multivariate biological index data 164-2 to calculate the person's severity level.

Next, the hazard prediction unit 137 extracts a contribution index contributing to the prediction of the accident risk using the predicted accident risk prediction data 166, the accident risk prediction model 171 used to predict the accident risk, the biological index data 164-2 of the driver ID to be analyzed, and the estimated person's severity level data 167, collates the contribution index, the person's severity level of the contribution index, the accident risk, and information on the accident risk prediction model 171, and stores the same in the combination table 168 (S107A).

By the above-described processing, the contribution index used to detect a hazardous state in a broad sense and give a warning, the person's severity level of the contribution index, the accident risk, and the accident risk prediction model information are stored in the combination table 168 at a predetermined timing such as after the biological index data 164-2 is updated.

The hazard prediction unit 137 may execute the processing of steps S113 and S114 in parallel or sequentially.

FIG. 25 is a flowchart showing an example of warning presentation processing performed by the operation support server 1. This processing is executed at a predetermined timing such as every time the combination table 168 is updated.

The warning presentation unit 138 reads an issuance definition which is a condition of presenting a warning from the alert definition data 172 (S141). A plurality of issuance definitions may be set according to the accident risk prediction model 171 and the biological state estimation model 169. Further, a plurality of issuance definitions may be set depending on a target of warning presentation and a method thereof, such as using a voice notification of the prediction result notification device 9 with respect to a driver, displaying a warning on a display, displaying a warning on the display of the input and output device 5 of a driver manager, and using an E-mail notification via the input and output device 5.

The warning presentation unit 138 refers to the accident risk and the person's severity level of each record in the combination table 168 (S142), and determines presence of a driver exceeding a threshold value set in the issuance definition (S107B).

The warning presentation unit 138 generates a countermeasure plan included in the warning to be given when there is a driver exceeding the threshold value and corresponding to the issuance definition (S107C). The countermeasure plan is generated by referring to the countermeasure plan data 173 corresponding to the contribution index in the combination table 168.

In addition, in order to increase warning acceptability of the driver receiving a warning, the warning presentation unit 138 may use the person's severity level of the contribution index in the combination table 168 to add information indicating how abnormal the state of the driver himself or herself is to the countermeasure plan. For example, the warning presentation unit 138 may add information indicating, for example, "this state occurs only once every N years".

Furthermore, the warning presentation unit 138 can add, to the countermeasure plan, information based on the business and environment data 174, the attribute information data 175, and the combination table 168. For example, the warning presentation unit 138 may update contents to be fed back as a countermeasure plan based on information on time N at which an accident risk is considered to increase from the information on the accident risk prediction model 171 stored in the combination table 168. Additionally, for example, the warning presentation unit 138 may update the contents of the feedback based on the weather and temperature information stored in the business and environment data 174.

The warning presentation unit 138 acquires a vehicle ID to be transmitted from a driver ID based on the business and environment data 174, and sets the vehicle 7 as a transmission target. When the transmission target is a driver manager instead of a driver, the warning presentation unit 138 may specify a manager ID instead of acquiring the vehicle ID, and may set the input and output device 5 of the operation support server 1 operated by the manager as the transmission target.

Thereafter, the warning presentation unit 138 transmits a warning to the generated countermeasure plan as an alert or a message to which an accident risk alert based on issuance definition corresponding to the issuance determination is added (S108).

A warning is transmitted to a vehicle of a driver detected as a hazardous state in a broad sense, by the above-described processing. In the vehicle 7 receiving the warning, the prediction result notification device 9 notifies the driver of the warning. Further, in the operation support server 1, the warning presentation unit 138 displays the vehicle to which the warning is transmitted on the display of the input and output device 5.

FIG. 26A and FIG. 26B are diagrams showing an example of a warning presentation screen outputted by the prediction result notification device 9. The prediction result notification device 9 has a display (not shown), and when receiving a warning from the operation support server 1, the prediction result notification device 9 displays a warning presentation screen 1000A. The warning presentation screen 1000A includes an area 1010 in which an accident risk alert is displayed, and a comment area 1020 in which a countermeasure plan or the like to avoid a hazardous state in a broad sense is displayed.

In the area 1010 in which the accident risk alert is displayed, for example, in addition to a warning statement 1011 of the accident risk increase, information 1012 based on the person's severity level of the biological index data 164-2 of the contribution index is displayed, thereby making it possible not only to simply notify that a driver is in a hazardous state, but also to give a warning in a form understandable to the driver himself or herself based on the person's severity level of the contribution index, such as "this state occurs only once every six months to you". Accordingly, it is expected that an acceptance degree of a driver with respect to a warning will be improved.

In the display of the information 1012 based on the person's severity level, the display thereof may be performed so as to understand whether the display is based on the biological state estimation model 169 generated only from the biological index data 164-2 of a target driver himself or herself, or whether the display is based on the biological state estimation model 169 generated from the biological index data of a plurality of drivers showing biological response characteristics similar to the target driver.

For example, on a warning presentation screen 1000B in FIG. 26B, information 1012B based on the person's severity level in the area 1010 in which the accident risk alert is displayed may be displayed in a text showing that the driver himself or herself is compared with the data of a plurality of driver, such as "this state occurs only once every six months to a driver similar to you".

Further, for example, when the driver himself or herself is compared with a plurality of drivers, information 1013 on which group of drivers are being compared with you may be displayed so as to recognize the comparison therebetween. Further, an icon or the like may be displayed to indicate which biological state estimation model 169 is being used. As described above, it is expected to obtain an effect of making it easier for a driver to perceive a warning as "his or her own affair".

Furthermore, in the comment area 1020 of the warning presentation screens 1000A and 1000B, for example, an interpretation 1021 of a physiological state based on a contribution index and a specific countermeasure plan 1022 to avoid a hazardous state in a broad sense are presented. In this manner, a driver receiving a warning presentation does not finish his or her action after receiving the warning. Further, the driver can understand an action to be taken next to eliminate the hazardous state and perform the action.

In this example, an example of presenting a warning by a warning presentation screen is shown, but a waning may be presented by other methods. For example, a warning may be given in the form of mechanically reading aloud a sentence having the same content as a content displayed on the warning presentation screen.

<Data Structure>

Next, a characteristic structure of each piece of data used in the operation support system is shown.

FIG. 27A is an example of a data structure of the biological index data 164 stored in the operation support system of the present invention. In addition to a driver ID 1401, a vehicle ID 1402, a date and time 1403, various autonomic nervous function indexes calculated by the biological index calculation unit 131 are stored in the biological index data 164. Here, examples of the autonomic nervous function index include LF/HF 1404 which is a frequency-domain index, an average heart rate 1405 which is a time-domain index, NN50 1406, or α1 1407 which is an RRI nonlinear-domain index.

FIG. 27B is an example of a data structure of the business and environment data 174 stored in the operation support system of the present invention. The business and environment data 174 stores business information during business of a driver and traveling environment information.

Typically, in addition to a driver ID 411, a start date and time 412 and an end date and time 413 indicating the duration of the information, and a vehicle ID 414 in use, for example, a vehicle type 415 indicating the size of a vehicle being driven, weather 416 and temperature 417 of a representative point in a traveling area, a business type 418 indicating a business state during the period from the start date and time 412 to the end date and time 413, and a business schedule 419 such as a destination are stored.

FIG. 27C is an example of a data structure of the attribute information data 175 stored in the operation support system of the present invention. The attribute information data 175 stores basic information on a driver having little time-varying (a change over time).

Typically, in addition to a driver ID 1421, a start date 1422 and an end date 1423 which are the duration to which basic information is applied, and a vehicle ID 1424 of a vehicle being used, for example, driving skill information measured by a driver aptitude test (example: a skill A 1425, pseudonym), personality temperament information measured by Temperament and Character Inventory (TCI) or the like (example: personality A 1426, pseudonym), gender 1427, age 1428, and driving experience 1429 are stored. In addition thereto, a biological state estimation model ID 1430, an accident risk prediction model ID 1431, and the like are stored therein as various model information preferentially used for a driver.

FIG. 27D is an example of a data structure of the learning information data 176 stored in the operation support system of the present invention. The learning information data 176 stores information to be used when the biological state estimation model 169 is generated, and typically stores a driver ID 1441, a start time 1441 and an end time 1443 which are period information of the biological index data 164 used for learning.

Further, the learning information data 176 may store a measurement condition 1444 of data of the period information for the purpose of arranging a measurement condition of data to be used for generation of the biological state estimation model 169. In this case, the measurement condition 1444 may be stored by the driving data collection device 10 configured to automatically discriminate the state from the in-vehicle sensor data 161-2 or the like (for example, high-speed traveling), or may be manually inputted (for example, lunch break) from conditions determined by a driver himself or herself via the business state input device 130.

When the biological state estimation model 169 is generated by a supervised model, in addition thereto, for example, a value 1445 obtained by measuring a degree of subjective fatigue by VAS may be stored as an objective variable necessary for generation of the supervised model.

FIG. 27E is an example of a data structure of the hazard occurrence data 162 stored in the operation support system of the present invention. The hazard occurrence data 162 stores data configured to set the type and occurrence date and time of a hazardous event detected by a driver, a driver manager, a commercially available in-vehicle warning device, and the like.

Typically, a vehicle ID 1451, an occurrence date and time 1452 of a hazardous event, and a hazard type 1453 are stored. An importance level 1454 of an event, configured to record seriousness of a situation of the detected hazardous event with visual confirmation or the like, may also be stored.

FIG. 27F is an example of a data structure of the accident risk prediction data 166 stored in the operation support system of the present invention.

The accident risk prediction data 166 stores an accident risk determined from the biological index data 164-2 using the accident risk prediction model 171. Typically, a driver ID 1461, a date and time 1462, an ID 1463 of the accident risk prediction model 171 used to predict an accident risk, and an accident risk 1464 indicating an occurrence probability (percentage) of a predicted hazardous event are stored in the accident risk prediction data 166.

FIG. 27G is an example of a data structure of the person's severity level data 167 stored in the operation support system of the present invention.

The person's severity level data 167 stores a person's severity level determined by the biological index data 164-2 using the biological state estimation model 169. Typically, a driver ID 1471, a date and time 1472, a type 1473 of the biological index data 164-2 estimating a person's severity level, an ID 1474 of the biological state estimation model 169 used for estimation, and a person's severity level 1475 are stored in the person's severity level data 167.

In addition, since the biological state estimation model 169 is generated for each biological index data type, and it is assumed that a calculation method of a person's severity level is also different for each biological index data type, an output format of the person's severity level is not necessarily constant.

For example, in the record on a first line, it is shown that the biological data type 1473 of the biological index data 164-2 outputs a statistic obtained by approximating an "average heart rate" with a normal distribution, and the person's severity level 1475 indicates a value of "+4SD" from the average using a standard deviation (SD).

Further, for example, in the record on a second line, it is shown that a quantile on a data distribution is outputted for NN50, and the person's severity level 1475 is a value corresponding to 99% quantile of the data set used for model construction.

FIG. 27H is an example of a data structure of the combination table 168 stored in the operation support system of the present invention. The combination table 168 is a table generated by collating values to be used in the warning presentation processing.

Typically, a driver ID 481, a vehicle ID 482, a date and time 483, an accident risk prediction model ID 484 used for prediction, a predicted accident risk 485, a contribution index 486 which is a biological index data type contributing to accident risk prediction, a biological state estimation model ID 487 used to estimate a biological state with respect to a contribution index, and a person's severity level 488 related to a contribution index are stored.

Furthermore, when it is determined that a certain record is in a hazardous state in a broad sense, an issued flag 489, which is a flag configured to manage whether the warning presentation unit 138 is already presented a warning, may be stored.

FIG. 27I is an example of a data structure of the alert definition data 172 stored in the operation support system of the present invention. The alert definition data 172 stores a determination condition to be used in determining whether a state corresponds to a hazardous state in a broad sense.

Typically, an alert ID 1491, an accident risk threshold value 1492, and a person's severity level threshold value 1493 are stored. In addition thereto, for example, a contribution index condition 1494 configured to additionally limit a contribution index in using the person's severity level threshold value 1493, a weather condition 1495 configured to limit target weather during business, and a person's severity level type 1496 configured to limit a determination target to only a person's severity level obtained in a specific output format when alert determination is executed may be stored.

FIG. 27J is an example of a data structure of the countermeasure plan data 173 stored in the operation support system of the present invention. The countermeasure plan data stores information to be used for generation of a countermeasure plan in warning presentation.

Typically, a plan ID 1501 of a countermeasure plan, a contribution index 1502 which is a condition to present the countermeasure plan, a phenomenon 1503 configured to indicate a state of a contribution index, an interpretation 1504 of a physiological state of a driver assumed from the phenomenon of the contribution index, and a countermeasure plan 1505 configured to avoid the corresponding hazardous state in a broad sense are stored.

For example, a plurality of countermeasure plans 1505 may be set for the same contribution index 1502, the phenomenon 1503, and the interpretation 1504. In this case, a priority 1506 configured to present the countermeasure plan 1505 may be further stored.

As described above, the operation support system of the embodiment detects whether a state corresponds to a hazardous state in a broad sense based on the accident risk prediction data 166 calculated by inputting the biological index data 164-2 calculated by the operation support server 1 from the heart rate data of the biological sensor 12 to the accident risk prediction model 171, and the person's severity level data 167 calculated by inputting the biological index data 164-2 to the biological state estimation model 169.

Thus, the operation support server 1 of the embodiment can detect a hazardous state before the hazardous state appears in the behavior of the vehicle 7 after absorbing individual differences in the biological index data 164-2. In addition, when a state corresponds to a hazardous state in a broad sense, the operation support server 1 presents a warning including a countermeasure plan to avoid a hazardous state in a broad sense based on a contribution index contributing to the prediction of an accident risk, thereby enabling a driver himself or herself receiving the warning to take a necessary action to avoid the hazardous state in the broad sense. As described above, the operation support server 1 makes it possible for a driver of the vehicle 7 to avoid a hazardous state in a broad sense in advance.

Although the third embodiment shows an example in which the present invention is applied to the operation support system configured to manage the vehicle 7, the present invention is not limited thereto. For example, instead of the vehicle 7, the present invention can be applied to a moving body requiring a driver or a pilot, such as a railway vehicle, a ship, or an aircraft.

Fourth Embodiment

Next, a fourth embodiment of the present invention will be described. Except for the differences described below, each unit of an operation support system in the fourth embodiment has the same function as that of each unit having the same reference numeral in the third embodiment, so a description thereof will be omitted.

FIG. 28 is a diagram showing an outline of processing performed by the operation support system of the fourth embodiment. In the fourth embodiment of the present invention, it is described that calculation is performed in consideration of individual differences in biological index data when an accident risk is estimated.

The biological index data 164-1 is inputted to the biological state estimation model 169 to calculate a person's severity level data 167A (a first person's severity level) (S106C), and the calculated person's severity level data 167A is inputted to the accident risk prediction model generation unit 135.

The accident risk prediction model generation unit 135 generates the accident risk prediction model 171 by inputting the person's severity level data 167A as well as the biological index data 164-1 and the accident risk estimation data 165 (S104).

Then, the hazard prediction unit 137 inputs the biological index data 164-2 to the biological state estimation model 169 to calculate a person's severity level data 167B (a second person's severity level) (S106B), and outputs the person's severity level data 167B to the accident risk estimation unit 133. The accident risk estimation unit 133 inputs the person's severity level data 167B as well as the biological index data 164-2 to the accident risk prediction model 171 (S106A).

Processing in which the hazard prediction unit 137 in step S107A extracts a contribution index using the person's severity level data 167B to generate the combination table 168 is the same as in the third embodiment.

Therefore, in the extraction and combination processing of the contribution index performed by the hazard prediction unit 137, the input contributing to the accident risk estimation is selected from the biological index data 164-2 and the person's severity level data 167B and set as the contribution index, the person's severity level of the biological index data 164-2 of the selected type is stored in the combination table 168 when the biological index data 164-2 is selected, and the person's severity level data 167B of the selected type is stored in the combination table 168 even when the person's severity level data 167B is selected.

As described above, in the fourth embodiment, in addition to the determination of the warning presentation described above, it is possible to estimate an accident risk in consideration of individual differences of the biological index data 164 even in the accident risk estimation, thereby having an effect of making it possible to predict an accident risk with higher accuracy.

Fifth Embodiment

Next, a fifth embodiment of the present invention will be described. Except for the differences described below, each unit of an operation support system in the fifth embodiment has the same function as that of each unit having the same reference numeral in the third embodiment, so a description thereof will be omitted.

FIG. 29 is a diagram showing an outline of processing performed by the operation support system of the fifth embodiment. In FIG. 29, the learning phase is omitted from the processing outline in FIG. 19, and the outline of the processing will be described for a difference in the operation phase.

In the operation support server 1 of the fifth embodiment, the warning presentation unit 138 does not perform the warning presentation every time after the hazard prediction unit 137 adds a record to the combination table 168, and the warning presentation unit 138 provides a list of warning presentation targets to a driver manager, thereby allowing the driver manager to intervene to manually support the operation of a driver.

Every time the hazard prediction unit 137 of the operation support server 1 updates the combination table 168, or at a fixed cycle, the warning presentation unit 138 reads the combination table 168 and updates an intervention candidate having a possibility of causing the driver manager to intervene (S115). For example, in the combination table 168, only the record group of the latest N hours on the day of operation in which the issued flag 489 is not "completed" is extracted.

After that, the warning presentation unit 138 performs issuance determination with respect to the extracted record group by the above-described method, and extracts a record group corresponding to a hazardous state in a broad sense (S107B). When the record group corresponding to the hazardous state in the broad sense exists, the warning presentation unit 138 generates a countermeasure plan to avoid the hazardous state in the broad sense for each of the record groups (S107C).

The warning presentation unit 138 displays a list of warning destinations, which is the record group in which the countermeasure plan is generated, on the display of the input and output device 5 (S116). In the list display of warning destinations, the warning destination considered to require manual intervention by the driver manager is preferentially displayed at the top, and intervention by the driver manager can be performed.

For example, the warning presentation unit 138 can compare the business and environment data 174 with the record group corresponding to the hazardous state in the broad sense, and can list and display, at the top, the record group in which the presented countermeasure plan cannot be taken at the discretion of a driver himself or herself for business reasons.

The input and output device 5 receives the intervention to the driver by the driver manager based on the list of warning destinations displayed on the display thereof (S117). For example, in the case of a driver who receives a message, as a countermeasure plan, indicating that "please take a rest at a nearby resting point" at a place where there is no resting point nearby, and who is running out of time to deliver packages, the driver manager uses an interface for voice communication with the driver displayed in the list of warning destinations, thereby making it possible to confirm the state of the driver himself or herself.

When it is confirmed that the driver does not need to take a rest immediately, the driver manager guides a point at which the driver can take a rest after the end of delivery, thereby making it possible to present the next best countermeasure plan to the driver.

Further, for example, in the case of a driver who is often warned that "you are getting drowsy and need a rest", when the driver manager confirms the state of the driver himself or herself and determines that it is difficult for the driver to carry out the original business schedule, the driver manager omits a part of the business scheduled for the second half of the business schedule on the day and a part of the business scheduled for the first thing in the morning of the next day, thereby making it possible to adjust the amount of work of the driver and allow the driver to take a rest.

FIG. 30 is a diagram showing an example of a warning destination list screen 2000 outputted by the display of the input and output device 5. When an intervention candidate extracted by the warning presentation unit 138 is updated and a countermeasure plan is generated, the input and output device 5 updates a list of warning destinations and displays the same on the warning destination list screen 2000.

A current time 2001 and a manager ID 2002 which is an ID of a driver manager who is browsing the warning destination list screen 2000 are displayed at the top portion of the warning destination list screen 2000. In a list of warning destinations 2003, a record group in which a countermeasure plan extracted and generated by the warning presentation unit 138 is generated is displayed in a tabular form. By pressing a downward triangular button in the drawing for each column, the record group can be sorted by prioritizing elements that the driver manager wishes to prioritize and confirm.

Details of a driver corresponding to a record selected by the driver manager to take an action are displayed in a lower area 2005. In the illustrated example, information on a corresponding driver ID "ZAX001" is displayed in a record 2004 in the list of warning destinations 2003.

The area 2005 displays a current position 2011 showing a position of the driver on the map, a countermeasure plan 2012 related to the selected record 2004, a business schedule 2013 of the driver, and a remark 2014 indicating the business status of a driver, and a driver contact button 2015 configured to directly communicate with a driver. In addition thereto, the time transition of the biological index data 164 related to the contribution index on the day may be displayed together.

In the current position 2011 of the driver, a position 2021 of a target driver, a traveling route result 2022 (a solid line) on the day, and a scheduled traveling route 2022 (a dotted line) are shown on the map. Further, the positions 2023 of other drivers around the driver are also displayed on the map.

A driver manager refers to the record 2004, the countermeasure plan 2012, and the business schedule 2013, and determines whether a driver can execute a countermeasure plan at his or her own discretion or whether it is necessary to directly confirm the status of the driver through the warning destination list screen 2000. Then, the driver manager can manually intervene to avoid a hazardous state in a broad sense by directly interacting with the driver by pressing the driver contact button 2015, as necessary.

As described above, the driver manager executes the countermeasure plan 2012 that is difficult to execute at the discretion of the driver himself or herself, or executes the next best countermeasure plan different from the countermeasure plan 2012, thereby making it possible to avoid a hazardous state in a broad sense and support the safe operation of a group of managed drivers.

As described above, in the fifth embodiment, regarding a countermeasure plan that is difficult to be implemented at the discretion of a driver who is in a hazardous state in a broad sense, a driver manager gives the driver permission for implementation of the countermeasure plan based on the state of the driver himself or herself. Accordingly, the driver can take a more fundamental countermeasure plan to avoid a hazardous state in a broad sense. As a result, the operation support system has an effect of making it possible to allow a driver to take a more flexible countermeasure plan and avoid a hazardous state in a broad sense.

According to the third to fifth embodiments, a hazardous state in a broad sense (a hazardous event) can be detected based on an accident risk prediction model, a biological state estimation model, and biological data. As a result, it is possible to determine the necessity of issuing a notification based on a hazardous state in a broad sense, and it is also possible to provide a countermeasure plan to avoid a hazardous state in a broad sense.

<Conclusion>

As described above, the operation support methods in the first and second embodiments can be configured as follows.

(1) An operation support method configured to support operation of a vehicle (7) by a computer including a processor (2) and a memory (3), includes: a first step of inputting, by the computer, first in-vehicle sensor data (40-$m$1) indicating a traveling state of the vehicle, the first in-vehicle sensor data being collected in the past, and hazard occurrence data (45) having information on hazard occurrence from the first in-vehicle sensor data (40-$m$1) preset therein, and generating, by the computer, an accident risk definition model (48) configured to estimate a probability of the hazard occurrence by machine learning as an accident risk; a second step of inputting, by the computer, second in-vehicle sensor data (40-$m$2) indicating the traveling state of the vehicle (7), the second in-vehicle sensor data (40-$m$2) being collected in the past, to the accident risk definition model (48), and generating, by the computer, accident risk estimation data (50) by estimating the probability of the hazard occurrence; a third step of inputting, by the computer, first biological index data (46-$m$) and the accident risk estimation data (50), wherein the first biological index data (46-$m$) is calculated in advance from first biological sensor data (the biological sensor data 41) of a driver when the second in-vehicle sensor data (40-$m$2) is collected, and generating, by the computer, an accident risk prediction model (43) by machine learning, wherein the accident risk prediction model (43) predicts an accident risk after a predetermined time; a fourth step of acquiring, by the computer, second biological sensor data (41) of a driver who is driving the vehicle (7), and calculating, by the computer, second biological index data (46) indicating a state of the driver from the second biological sensor data (41); and a fifth step of inputting, by the computer, the second biological index data (46) to the accident risk prediction model (43), and predicting, by the computer, the accident risk (444) after the predetermined time Δt.

According to the above configuration, the operation support server 1 can predict the accident risk after the predetermined time Δt from the first biological data (the biological sensor data 41) of the driver who is driving the vehicle 7.

(2) The operation support method according to (1) further includes a sixth step of generating and outputting, by the computer, an alert when a predicted value of the accident risk after the predetermined time Δt is equal to or greater than a preset threshold value Th.

According to the above configuration, the operation support server 1 predicts that the accident risk is equal to or greater than the threshold value Th after the predetermined time Δt, and notifies the prediction result notification device 9 of the corresponding vehicle 7 and the display of the input and output device 5 of the prediction, thereby making it possible to cause a driver and a manager to be careful of an accident risk with an alert and a message before the accident risk increases. Accordingly, the operation support server 1 can promote the safe operation of each vehicle 7.

(3) In the operation support method according to (1), the fourth step includes a step of acquiring heart rate data of the driver as the second biological sensor data (41), a step of calculating an RRI from the heart rate data and generating heart rate variability time-series data, a step of performing frequency spectral analysis of the heart rate variability time-series data, and a step of calculating, from a result of the frequency spectral analysis, autonomic nerve total power from the sum of an intensity LF of a low-frequency component of power spectral density and an intensity HF of a high-frequency component thereof and calculating the same as biological index data (the autonomic nerve total power 462).

According to the above configuration, the time-series heart rate variability data is calculated from the heart rate data of the biological sensor data 41, and the intensities (LF and HF) of the low-frequency component and the high-frequency component are calculated, thereby obtaining the autonomic nerve total power 462 and the autonomic nerve LF/HF 463.

(4) In the operation support method according to (3), the fifth step inputs the intensity (LF) of the low-frequency component of the power spectral density and the intensity (HF) of the high-frequency component thereof to the accident risk prediction model (43), and causes the accident risk prediction model (43) to output interpretation data indicating the state of the driver.

According to the above configuration, it is known that when the sympathetic nerve is activated, a driver is in a stressed state, and when the parasympathetic nerve is activated, a driver is in a relaxed state, so it is possible to determine whether the driver is in the stressed state or in the relaxed state from the intensity LF of the low-frequency component and the intensity HF of the high-frequency component.

(5) In the operation support method according to (2), the sixth step acquires position information (the position 402) of the vehicle (7), and outputs a screen (the prediction result display screen 600) configured to display the position information (402) of the vehicle (7) and information (603) indicating the state of the driver.

According to the above configuration, a manager can confirm accident risks of a plurality of drivers by listing the same on the map, and can select a driver having a high accident risk and remotely give an instruction to the driver.

(16) In the operation support method according to (1), the fourth step includes a step of acquiring heart rate data of the driver as the first biological sensor data (41), a step of calculating an RRI from the heart rate data and generating heart rate variability time-series data, a step of calculating a difference value of the adjacent RRI with respect to the heart rate variability time-series data and generating a difference series ΔRRI(t), and a step of calculating the total number of difference values from the difference series ΔRRI(t) as an autonomic nerve NNXX and using the autonomic nerve NNXX as the biological index data (462), wherein the difference values are equal to or greater than a predetermined value XX msec.

According to the above configuration, the time-series heart rate variability data is calculated from the heart rate data of the biological sensor data 41, the difference series ΔRRI(t) is calculated from the heart rate variability data, and the total number of difference values, the difference values being equal to or greater than a predetermined value XX msec, is calculated as the autonomic nerve NNXX, thereby making it possible to obtain the biological index data 46 as an index indicating the magnitude of parasympathetic nerve activity.

Further, the operation support server 1 according to the third to fifth embodiments can be configured as follows.

(19) An operation support method configured to support operation of a vehicle (7) by a computer (the operation support sever 1) including a processor (2) and a memory (3), includes: a first step of inputting, by the computer (1), first in-vehicle sensor data (161-1) indicating a traveling state of the vehicle (7) collected in the past and preset hazard occurrence data (162), and generating, by the computer (1), an accident risk definition model (170) configured to estimate a probability of occurrence of a hazardous event as an accident risk; a second step of inputting, by the computer, second in-vehicle sensor data (161-2) indicating a traveling state of the vehicle (7) collected in the past to the accident risk definition model (170), and generating, by the computer, accident risk estimation data (165) by estimating a probability of occurrence of a hazardous event; a third step of inputting, by the computer, first biological index data (164-1) and the accident risk estimation data (165), wherein the first biological index data (164-1) is calculated in advance from first biological sensor data (the biological sensor data 163) of a driver when the second in-vehicle sensor data (161-2) is collected, and generating, by the computer, an accident risk prediction model (171) configured to predict an accident risk after a predetermined time; a fourth step of inputting, by the computer, third biological index data (164-3) calculated in advance, and generating, by the computer, a biological state estimation model (169) configured to calculate a person's severity level (the person's severity level data 167); a seventh step of acquiring, by the computer, the second biological sensor data (163) of the driver who is driving the vehicle (7) from a biological sensor (12) of the vehicle (7), and calculating, by the computer, the second biological index data (164-2) indicating the state of the driver from the second biological sensor data (163); an eighth step of inputting, by the computer, the second biological index data (164-2) to the accident risk prediction model (171) to predict the accident risk, and inputting, by the computer, the second biological index data (164-2) to the biological state estimation model (169) to calculate the person's severity level (167); and a ninth step of determining, by the computer, whether a warning is issued based on the predicted accident risk (the accident risk prediction data 166) and the calculated person's severity level (167).

According to the above configuration, the operation support server 1 can detect a hazardous state (a hazardous event) in a broad sense based on the accident risk prediction model 171, the biological state estimation model 169, and the biological index data 164.

(20) The operation support method according to (19) further includes a tenth step of extracting, by the computer, the accident risk prediction model (171), the accident risk (166), and a contribution index which is the biological data type contributing to prediction of the accident risk (166) when the warning is determined to be issued, and an eleventh step of generating, by the computer, a countermeasure plan to avoid a hazardous event based on the person's severity level (167) related to the contribution index.

According to the above configuration, the operation support server 1 detects a hazardous state (a hazardous event) in a broad sense based on the accident risk prediction model 171, the biological state estimation model 169, and the biological index data 164, thereby making it possible to provide a countermeasure plan to avoid a hazardous state in a broad sense when a warning is issued.

(21) The operation support method according to (20) further includes a twelfth step of generating and outputting, by the computer, a warning including the countermeasure plan (the countermeasure plan data 173) to avoid the hazardous event.

According to the above configuration, the operation support server 1 detects a hazardous state (a hazardous event) in a broad sense based on the accident risk prediction model 171, the biological state estimation model 169, and the biological index data 164, thereby making it possible to generate a countermeasure plan to avoid a hazardous state in a broad sense and give a warning when the warning is issued.

(22) In the operation support method according to (19), in the fourth step, the biological state estimation model (169) configured to calculate the person's severity level (167) is generated by inputting the third biological index data (164-3) and learning information data (176) including at least a target period to be used in generating the biological state estimation model (169) among the third biological index data (164-3).

According to the above configuration, when selecting the biological index data 164-3 to be inputted for clustering, the biological state estimation model generation unit 134 may select only the biological index data 164-3 measured under the same measurement conditions based on the learning information data 176, and may input only the biological index data 164-3 in the period stored in the learning information data 176. Accordingly, it is expected that measurement conditions are controlled and thus variations in the biological index data 164-3 are prevented.

(23) In the operation support method according to (20), in the eighth step, a combination table (168) is generated, wherein the combination table (168) stores the accident risk (166), the contribution index, and the person's severity level (167) related to the contribution index in association with each other.

According to the above configuration, the contribution index used to detect a hazardous state in a broad sense and give a warning, the person's severity level of the contribution index, the accident risk, and the accident risk prediction model information are stored in the combination table 168 at a predetermined timing such as after the biological index data 164-2 is updated.

(24) In the operation support method according to (21), in the twelfth step, information based on the person's severity level (167) and the warning including the countermeasure plan (173) to avoid the hazardous event are displayed.

According to the above configuration, in the area 1010 in which the accident risk alert is displayed, for example, in addition to the warning statement 1011 of the accident risk increase, the information 1012 based on the person's severity level of the biological index data 164-2 of the contribution index is displayed. In this manner, it is possible not only to notify that a driver is in a hazardous state, but also to give a warning in a form understandable to the driver himself or herself based on the person's severity level of the contribution index, such as "this state occurs only once every six months to you". Accordingly, it is expected that an acceptance degree of a driver with respect to a warning will be improved.

(25) The operation support method according to (19) further includes a thirteenth step of inputting, by the computer, the first biological index data (164-1) to the biological state estimation model (169) to calculate a first person's severity level (167A), wherein, in the third step, the first biological index data (164-1) calculated in advance from the first biological sensor data (163) of the driver when the second in-vehicle sensor data (161-2) is collected, the accident risk estimation data (165), and the first person's severity level (167A) are inputted to generate an accident risk prediction model (171) configured to predict the accident risk (166) after the predetermined time, and, in the eighth step, the second biological index data (164-2) is inputted to the biological state estimation model (169) to calculate a second person's severity level (167B), and the second biological index data (164-2) and the second person's severity level (167B) are inputted to the accident risk prediction model (171) to predict the accident risk (166).

According to the above configuration, in addition to the determination of the warning presentation, it is possible to estimate an accident risk in consideration of individual differences of the biological index data 164 even in the accident risk estimation using the biological index data 164, thereby having an effect of making it possible to predict an accident risk with higher accuracy.

The present invention is not limited to the embodiments described above, but includes various modifications. For example, the embodiments are described in detail to describe the present invention in an easy-to-understand manner, and are not necessarily limited to those having all the configurations described herein. A part of a configuration of one embodiment can be replaced with a configuration of another embodiment, and the configuration of another embodiment can be added to the configuration of one embodiment. Further, for a part of the configuration of each embodiment, any addition, deletion, or replacement of other configurations can be applied alone or in combination thereof.

Furthermore, some or all of the above configurations, functions, processing units, processing means, and the like, may be implemented by hardware by designing, for example, an integrated circuit. Furthermore, the respective configurations, functions, and the like may be implemented by software by allowing a processor to interpret and execute a program configured to implement the respective functions thereof. Information on a program, a table, a file, and the like that implement each function can be stored in a recording device such as a memory, a hard disk, a solid state drive (SSD), or in a recording medium such as an IC card, an SD card, and a DVD.

In addition, a control line and an information line indicate what is considered necessary for description, and do not necessarily indicate all control lines and information lines on the product. In fact, it may be considered that almost all the configurations are connected to each other.

The invention claimed is:

1. An operation support method configured to support operation of a vehicle by a computer including a processor and a memory, the method comprising:
   obtaining, by the computer, first in-vehicle sensor data indicating a traveling state of the vehicle, the first in-vehicle sensor data being collected in a prior period, and hazard occurrence data having information on hazard occurrence from the first in-vehicle sensor data;
   generating, by the computer, an accident risk definition model configured to estimate a probability of the hazard occurrence by machine learning as an accident risk;
   receiving, by the computer, second in-vehicle sensor data indicating the traveling state of the vehicle, the second in-vehicle sensor data being collected in the prior period, to the accident risk definition model;

generating, by the computer, accident risk estimation data by estimating the probability of the hazard occurrence;

receiving, by the computer, first biological index data and the accident risk estimation data, wherein the first biological index data is calculated in advance from first biological sensor data of a driver when the second in-vehicle sensor data is collected;

generating, by the computer, an accident risk prediction model by the machine learning, wherein the accident risk prediction model predicts the accident risk after a predetermined time;

acquiring, by the computer, second biological sensor data of the driver who is driving the vehicle;

calculating, by the computer, second biological index data indicating a state of the driver from the second biological sensor data; and predicting, by the computer, the accident risk after the predetermined time by inputting the second biological index data to the accident risk prediction model, wherein the acquiring includes:
acquiring heart rate data of the driver as the second biological sensor data,
calculating an RRI from the heart rate data and generating heart rate variability time-series data,
performing frequency spectral analysis of the heart rate variability time-series data, and
calculating, from a result of the frequency spectral analysis, a sum of an intensity of a low-frequency component of power spectral density and an intensity of a high-frequency component thereof as an autonomic nerve total power, and using the autonomic nerve total power as the biological index data.

2. The operation support method according to claim 1, further comprising:
generating and outputting, by the computer, an alert when a predicted value of the accident risk after the predetermined time is equal to or greater than a preset threshold value.

3. The operation support method according to claim 1, wherein,
the intensity of the low-frequency component of the power spectral density and the intensity of the high-frequency component are inputs to the accident risk prediction model, and
the accident risk prediction model outputs interpretation data indicating the state of the driver.

4. The operation support method according to claim 2, further comprising
acquiring position information of the vehicle, and outputting a screen configured to display the position information of the vehicle and information indicating the state of the driver.

5. The operation support method according to claim 1, wherein,
the acquiring further includes
calculating a difference value of an adjacent RRI with respect to the heart rate variability time-series data and generating a difference series ΔRRI(t), and
calculating a total number of difference values from the difference series ΔRRI (t) as an autonomic nerve NNXX and using the autonomic nerve NNXX as the second biological index data, wherein the difference values are equal to or greater than a predetermined value XX msec.

6. An operation support system configured to support operation of a vehicle, the operation support system comprising:
a memory;
a communication interface that is communicatively coupled to an in-vehicle sensor, wherein the in-vehicle sensor is configured to detect a traveling state and a biological sensor configured to detect biological sensor data of a driver; and
a processor that is communicatively coupled to memory and the communication interface, wherein the processor is configured to:
receive a first input from the in-vehicle sensor indicating the traveling state of the vehicle, the first input being collected in a prior period, and hazard occurrence data having information on hazard occurrence from the first input,
generate an accident risk definition model configured to estimate a probability of the hazard occurrence by machine learning as an accident risk,
receive a second input from the in-vehicle sensor indicating the traveling state of the vehicle, the second input being collected in the prior period, to the accident risk definition model,
generate accident risk estimation data by estimating the probability of the hazard occurrence,
receive an input of first biological index data and the accident risk estimation data, wherein the first biological index data is calculated in advance from first biological sensor data acquired as the biological sensor data of the driver when the second input is collected,
generate an accident risk prediction model by the machine learning, wherein the accident risk prediction model predicts the accident risk after a predetermined time,
acquire second biological sensor data of the driver who is driving the vehicle from the biological sensor of the vehicle, thereby calculating second biological index data indicating a state of the driver from the second biological sensor data, and
predict the accident risk after the predetermined time by inputting the second biological index data into the accident risk prediction model,
wherein the second input is received by:
acquiring heart rate data of the driver as the second biological sensor data,
calculating an RRI from the heart rate data and generating heart rate variability time-series data,
performing frequency spectral analysis of the heart rate variability time-series data, and
calculating, from a result of the frequency spectral analysis, a sum of an intensity of a low-frequency component of power spectral density and an intensity of a high-frequency component thereof as an autonomic nerve total power, and using the autonomic nerve total power as the second biological index data.

7. The operation support system according to claim 6, wherein the processor is further configured to:
generate and output an alert when a predicted value of the accident risk after the predetermined time is equal to or greater than a preset threshold value.

8. The operation support system according to claim 6, wherein the processor is further configured to:
input the intensity of the low-frequency component of the power spectral density and the intensity of the high-frequency component to the accident risk prediction model, and output interpretation data indicating the state of the driver.

9. The operation support system according to claim 7, wherein the processor is further configured to,
acquire position information of the vehicle from the in-vehicle sensor, and
output a screen configured to display the position information of the vehicle and information indicating the state of the driver.

10. The operation support system according to claim 6, wherein the processor is further configured to,
calculate a difference value of an adjacent RRI with respect to the heart rate variability time-series data to generate a difference series ΔRRI (t), and
calculate a total number of difference values from the difference series ΔRRI(t) as an autonomic nerve NNXX to use the autonomic nerve NNXX as the second biological index data, wherein the difference values are equal to or greater than a predetermined value XX msec.

11. An operation support method configured to support operation of a vehicle by a computer including a processor and a memory, the method comprising:
obtaining, by the computer, first in-vehicle sensor data indicating a traveling state of the vehicle, the first in-vehicle sensor data being collected in a prior period, and hazard occurrence data having information on hazard occurrence from the first in-vehicle sensor data;
generating, by the computer, an accident risk definition model configured to estimate a probability of the hazard occurrence by machine learning as an accident risk;
receiving, by the computer, second in-vehicle sensor data indicating the traveling state of the vehicle, the second in-vehicle sensor data being collected in the prior period, to the accident risk definition model;
generating, by the computer, accident risk estimation data by estimating the probability of the hazard occurrence;
receiving, by the computer, first biological index data and the accident risk estimation data, wherein the first biological index data is calculated in advance from first biological sensor data of a driver when the second in-vehicle sensor data is collected;
generating, by the computer, an accident risk prediction model by the machine learning, wherein the accident risk prediction model predicts the accident risk after a predetermined time;
acquiring, by the computer, second biological sensor data of the driver who is driving the vehicle;
calculating, by the computer, second biological index data indicating a state of the driver from the second biological sensor data;
predicting, by the computer, the accident risk after the predetermined time by inputting the second biological index data to the accident risk prediction model,
wherein receiving, by the computer, first biological index data and the accident risk estimation data further includes
calculating, by the computer, a severity level for the driver by obtaining third biological index data calculated in advance, and
generating, by the computer, a biological state estimation model configured to calculate a person's severity level;
acquiring, by the computer, the second biological sensor data of the driver who is driving the vehicle from a biological sensor of the vehicle;
calculating, by the computer, the second biological index data indicating the state of the driver from the second biological sensor data;
inputting, by the computer, the second biological index data to the accident risk prediction model to predict the accident risk;
inputting, by the computer, the second biological index data to the biological state estimation model to calculate the person's severity level; and
determining, by the computer, whether a warning is issued based on the accident risk predicted and the severity level calculated.

12. The operation support method according to claim 11, further comprising:
extracting, by the computer, the accident risk prediction model, the accident risk, and a contribution index which is a biological data type contributing to prediction of the accident risk when the warning is determined to be issued; and
generating, by the computer, a countermeasure plan to avoid a hazardous event based on the person's severity level related to the contribution index.

13. The operation support method according to claim 12, further comprising:
generating and outputting, by the computer, a warning including the countermeasure plan.

14. The operation support method according to claim 11, further comprising,
inputting the third biological index data and learning information data including at least a target period to be used in generating the biological state estimation model among the first biological index data.

15. The operation support method according to claim 12, further comprising,
generating, a combination table is generated, wherein the combination table stores the accident risk, the contribution index, and the person's severity level related to the contribution index in association with each other.

16. The operation support method according to claim 13, further comprising,
displaying severity level and the warning including the countermeasure plan are displayed.

17. The operation support method according to claim 11, further comprising:
inputting, by the computer, the first biological index data to the biological state estimation model to calculate the severity level, wherein,
the first biological index data, the accident risk estimation data, and the severity level are inputted to generate the accident risk prediction model configured to predict the accident risk after the predetermined time, wherein the first biological index data is calculated in advance from the first biological sensor data of the driver when the second in-vehicle sensor data is collected, and
the second biological index data is inputted to the biological state estimation model to calculate a second person's severity level, and the second biological index data and the second person's severity level are inputted to the accident risk prediction model to predict the accident risk.

18. An operation support system configured to support operation of a vehicle, the operation support system comprising:
a memory;
a communication interface that is communicatively coupled to an in-vehicle sensor, wherein the in-vehicle sensor is configured to detect a traveling state and a biological sensor configured to detect biological sensor data of a driver; and a processor that is communicatively coupled to memory and the communication interface, wherein the processor is configured to:

receive a first input from the in-vehicle sensor indicating the traveling state of the vehicle, the first input being collected in a prior period, and hazard occurrence data having information on hazard occurrence from the first input, generate an accident risk definition model configured to estimate a probability of the hazard occurrence by machine learning as an accident risk, receive a second input from the in-vehicle sensor indicating the traveling state of the vehicle, the second input being collected in the prior period, to the accident risk definition model, generate accident risk estimation data by estimating the probability of the hazard occurrence, receive an input of first biological index data and the accident risk estimation data, wherein the first biological index data is calculated in advance from first biological sensor data acquired as the biological sensor data of the driver when the second input is collected, generate an accident risk prediction model by the machine learning, wherein the accident risk prediction model predicts the accident risk after a predetermined time, acquire second biological sensor data of the driver who is driving the vehicle from the biological sensor of the vehicle, thereby calculating second biological index data indicating a state of the driver from the second biological sensor data, predict the accident risk after the predetermined time by inputting the second biological index data into the accident risk prediction model, generate a biological state estimation model configured to calculate a severity level of the driver by inputting third biological index data calculated in advance, predict the accident risk by inputting the second biological index data to the accident risk prediction model, calculate the severity level by inputting the second biological index data to the biological state estimation model, and determine whether a warning is issued based on the predicted accident risk and the calculated severity level.

19. The operation support system according to claim 18, wherein the processor is further configured to:

generate the accident risk prediction model, the accident risk, a contribution index which is a biological data type contributing to prediction of the accident risk, and a countermeasure plan to avoid a hazardous event based on the severity level related to the contribution index when the warning is determined to be issued.

20. The operation support system according to claim 19, wherein the processor is further configured to:

generate and output the warning including the countermeasure plan.

21. The operation support system according to claim 18, wherein the processor is further configured to:

generate the biological state estimation model configured to calculate the person's severity level by inputting the third biological index data and learning information data including at least a target period to be used in generating the biological state estimation model among the first biological index data.

22. The operation support system according to claim 19, wherein the processor is further configured to:

generate a combination table configured to store the accident risk, the contribution index, and the severity level related to the contribution index in association with each other.

23. The operation support system according to claim 18, wherein the processor is further configured to:

display information based on the severity level and the warning including a countermeasure plan to avoid a hazardous event.

24. The operation support system according to claim 18, wherein the processor is further configured to:

input the first biological index data to the biological state estimation model to calculate the severity level, input the first biological index data, the accident risk estimation data, and the severity level to generate the accident risk prediction model configured to predict the accident risk after the predetermined time, wherein the first biological index data is calculated in advance from the first biological sensor data of the driver when the second input is collected, input the second biological index data to the biological state estimation model to calculate a second person's severity level, and input the second biological index data and the second person's severity level to the accident risk prediction model to predict the accident risk.

25. A non-transitory computer readable storage medium storing instructions for supporting operation of a vehicle, the instructions when executed by a processor cause the processor to perform a method comprising:

obtaining first in-vehicle sensor data indicating a traveling state of the vehicle, the first in-vehicle sensor data being collected in a prior period, and hazard occurrence data having information on hazard occurrence from the first in-vehicle sensor data;

generating an accident risk definition model configured to estimate a probability of the hazard occurrence by machine learning as an accident risk;

receiving second in-vehicle sensor data indicating the traveling state of the vehicle, the second in-vehicle sensor data being collected in the prior period, to the accident risk definition model;

generating accident risk estimation data by estimating the probability of the hazard occurrence;

receiving first biological index data and the accident risk estimation data, wherein the first biological index data is calculated in advance from first biological sensor data of a driver when the second in-vehicle sensor data is collected;

generating an accident risk prediction model by the machine learning, wherein the accident risk prediction model predicts the accident risk after a predetermined time;

acquiring second biological sensor data of the driver who is driving the vehicle;

calculating second biological index data indicating a state of the driver from the second biological sensor data;

predicting the accident risk after the predetermined time by inputting the second biological index data to the accident risk prediction model, generating a biological state estimation model configured to calculate a person's severity level by inputting third biological index data calculated in advance;

predicting the accident risk by inputting the second biological index data to the accident risk prediction model, and to calculate the person's severity level by inputting the second biological index data to the biological state estimation model; and determining whether a warning is issued based on the predicted accident risk and the severity level.

26. The non-transitory computer readable storage medium according to claim 25, wherein the method further comprises, generating the accident risk prediction model, the accident risk, a contribution index which is a biological data type contributing to prediction of the accident risk, and a countermeasure plan to avoid a hazardous event based on the person's severity level related to the contribution index when the warning is determined to be issued.

27. The non-transitory computer readable storage medium according to claim 26, wherein the method further comprises, generating and outputting the warning including the countermeasure plan.

28. The non-transitory computer readable storage medium according to claim 25, wherein the method further comprises:

generating the biological state estimation model configured to calculate the severity level by inputting the third biological index data and learning information data including at least a target period to be used in generating the biological state estimation model among the first biological index data.

29. The non-transitory computer readable storage medium according to claim 26, wherein the method further comprises:

generating a combination table configured to store the accident risk, the contribution index, and the severity level related to the contribution index in association with each other.

30. The non-transitory computer readable storage medium according to claim 25, wherein the method further comprises:

displaying information based on the severity level and the warning including a countermeasure plan to avoid a hazardous event.

31. A non-transitory computer readable storage medium storing instructions for supporting operation of a vehicle, the instructions when executed by a processor cause the processor to perform a method comprising:

obtaining first in-vehicle sensor data indicating a traveling state of the vehicle, the first in-vehicle sensor data being collected in a prior period, and hazard occurrence data having information on hazard occurrence from the first in-vehicle sensor data;

generating an accident risk definition model configured to estimate a probability of the hazard occurrence by machine learning as an accident risk;

receiving second in-vehicle sensor data indicating the traveling state of the vehicle, the second in-vehicle sensor data being collected in the prior period, to the accident risk definition model;

generating accident risk estimation data by estimating the probability of the hazard occurrence;

receiving first biological index data and the accident risk estimation data, wherein the first biological index data is calculated in advance from first biological sensor data of a driver when the second in-vehicle sensor data is collected;

generating an accident risk prediction model by the machine learning, wherein the accident risk prediction model predicts the accident risk after a predetermined time;

acquiring second biological sensor data of the driver who is driving the vehicle;

calculating second biological index data indicating a state of the driver from the second biological sensor data; and predicting the accident risk after the predetermined time by inputting the second biological index data to the accident risk prediction model, wherein the acquiring includes:
acquiring heart rate data of the driver as the second biological sensor data,
calculating an RRI from the heart rate data and generating heart rate variability time-series data,
performing frequency spectral analysis of the heart rate variability time-series data, and
calculating, from a result of the frequency spectral analysis, a sum of an intensity of a low-frequency component of power spectral density and an intensity of a high-frequency component thereof as an autonomic nerve total power, and using the autonomic nerve total power as the second biological index data.

32. The non-transitory computer readable storage medium according to claim 31, further comprising:

generating and outputting an alert when a predicted value of the accident risk after the predetermined time is equal to or greater than a preset threshold value.

33. The non-transitory computer readable storage medium according to claim 31, wherein, the intensity of the low-frequency component of the power spectral density and the intensity of the high-frequency component thereof to the accident risk prediction model, and the accident risk prediction model outputs interpretation data indicating the state of the driver.

34. The non-transitory computer readable storage medium according to claim 32, further comprising, acquiring position information of the vehicle from an in-vehicle sensor, and outputting a screen configured to display the position information of the vehicle and information indicating the state of the driver.

35. The non-transitory computer readable storage medium according to claim 31, wherein the acquiring further comprises:

calculating a difference value of an adjacent RRI with respect to the heart rate variability time-series data to generate a difference series ΔRRI (t), and calculating a total number of difference values from the difference series ΔRRI(t) as an autonomic nerve NNXX to use the autonomic nerve NNXX as the second biological index data, wherein the difference values are equal to or greater than a predetermined value XX msec.

* * * * *